United States Patent
Naya et al.

(10) Patent No.: US 7,843,571 B2
(45) Date of Patent: Nov. 30, 2010

(54) SENSING SYSTEM

(75) Inventors: Masayuki Naya, Ashigarakami-gun (JP); Masami Hatori, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/088,848

(22) PCT Filed: Sep. 28, 2006

(86) PCT No.: PCT/JP2006/319921
§ 371 (c)(1),
(2), (4) Date: Mar. 31, 2008

(87) PCT Pub. No.: WO2007/037520
PCT Pub. Date: Apr. 5, 2007

(65) Prior Publication Data
US 2009/0231590 A1    Sep. 17, 2009

(30) Foreign Application Priority Data
Sep. 30, 2005 (JP) .............................. 2005-288481
Sep. 30, 2005 (JP) .............................. 2005-288482

(51) Int. Cl.
G01N 21/55 (2006.01)
G01N 21/00 (2006.01)
G01N 21/43 (2006.01)
G01B 9/02 (2006.01)

(52) U.S. Cl. ................. 356/445; 356/436; 356/517; 356/519; 422/82.09

(58) Field of Classification Search ............... None
See application file for complete search history.

(56) References Cited

U.S. PATENT DOCUMENTS

| 4,050,895 A | * | 9/1977 | Hardy et al. ............ 436/527 |
| 4,529,319 A | * | 7/1985 | Muller ................... 356/432 |
| 4,678,904 A |   | 7/1987 | Saaski et al. |

(Continued)

FOREIGN PATENT DOCUMENTS
JP    6135334 A    2/1986

(Continued)

OTHER PUBLICATIONS

Takayuki Okamoto et al., "Local plasmon sensor with the gold colloid monolayers deposited upon glass substrates", Optic Letters, 2000, pp. 372-374, vol. 25, Issue 6.

Primary Examiner—Tarifur Chowdhury
Assistant Examiner—Gordon J Stock, Jr.
(74) Attorney, Agent, or Firm—Sughrue Mion, PLLC

(57) ABSTRACT

A sensing system using a sensing element being constituted by a transparent body sandwiched by first and second reflectors one or each of which is in contact with a specimen, and exhibiting an absorption characteristic varying with the specimen. The first reflector is a partially transparent reflective, and the second reflector is completely reflective, or partially transparent reflective. A light injection unit injects light onto the first reflector, and a light detection unit detects the intensity of light outputted from the sensing element in response to the injection. The light injection unit has a wavelength stabilizing arrangement and injects laser light, or injects light at two wavelengths. In the latter case, the light detection unit detects the intensities of outputted light at the two wavelengths, and a calculation unit obtains the difference between the intensities.

3 Claims, 9 Drawing Sheets

U.S. PATENT DOCUMENTS

| | | | |
|---|---|---|---|
| 5,210,404 A * | 5/1993 | Cush et al. | 250/216 |
| 5,485,277 A * | 1/1996 | Foster | 356/445 |
| 5,955,729 A | 9/1999 | Nelson et al. | |
| 6,289,286 B1 | 9/2001 | Andersson et al. | |
| 7,351,588 B2 * | 4/2008 | Poponin | 436/171 |
| 7,359,048 B2 * | 4/2008 | Wang et al. | 356/301 |
| 7,403,292 B2 * | 7/2008 | Tomaru | 356/517 |
| 7,420,682 B2 * | 9/2008 | Salamon et al. | 356/445 |
| 7,545,549 B2 * | 6/2009 | Tomaru | 359/240 |
| 7,643,156 B2 * | 1/2010 | Naya et al. | 356/519 |
| 2002/0005953 A1 * | 1/2002 | Negami et al. | 356/445 |
| 2002/0109846 A1 * | 8/2002 | Naya | 356/445 |
| 2004/0183176 A1 | 9/2004 | Naya et al. | |
| 2004/0256563 A1 * | 12/2004 | Uchida et al. | 250/339.11 |
| 2006/0012795 A1 * | 1/2006 | Niemax et al. | 356/445 |
| 2006/0043301 A1 * | 3/2006 | Mantele et al. | 250/339.11 |
| 2009/0268205 A1 * | 10/2009 | Naya | 356/445 |

FOREIGN PATENT DOCUMENTS

| | | | |
|---|---|---|---|
| JP | 240537 A | | 2/1990 |
| JP | 05072119 A | * | 3/1993 |
| JP | 05142142 A | * | 6/1993 |
| JP | 6167443 A | | 6/1994 |
| JP | 7229829 A | | 8/1995 |
| JP | 08201279 A | * | 8/1996 |
| JP | 11512518 A | | 10/1999 |
| JP | 2002517720 A | | 6/2002 |
| JP | 2002277388 A | * | 9/2002 |
| JP | 2003527606 A | | 9/2003 |
| JP | 2004232027 A | | 8/2004 |
| JP | 2005321244 A | | 11/2005 |
| WO | 0169258 A1 | | 9/2001 |

* cited by examiner

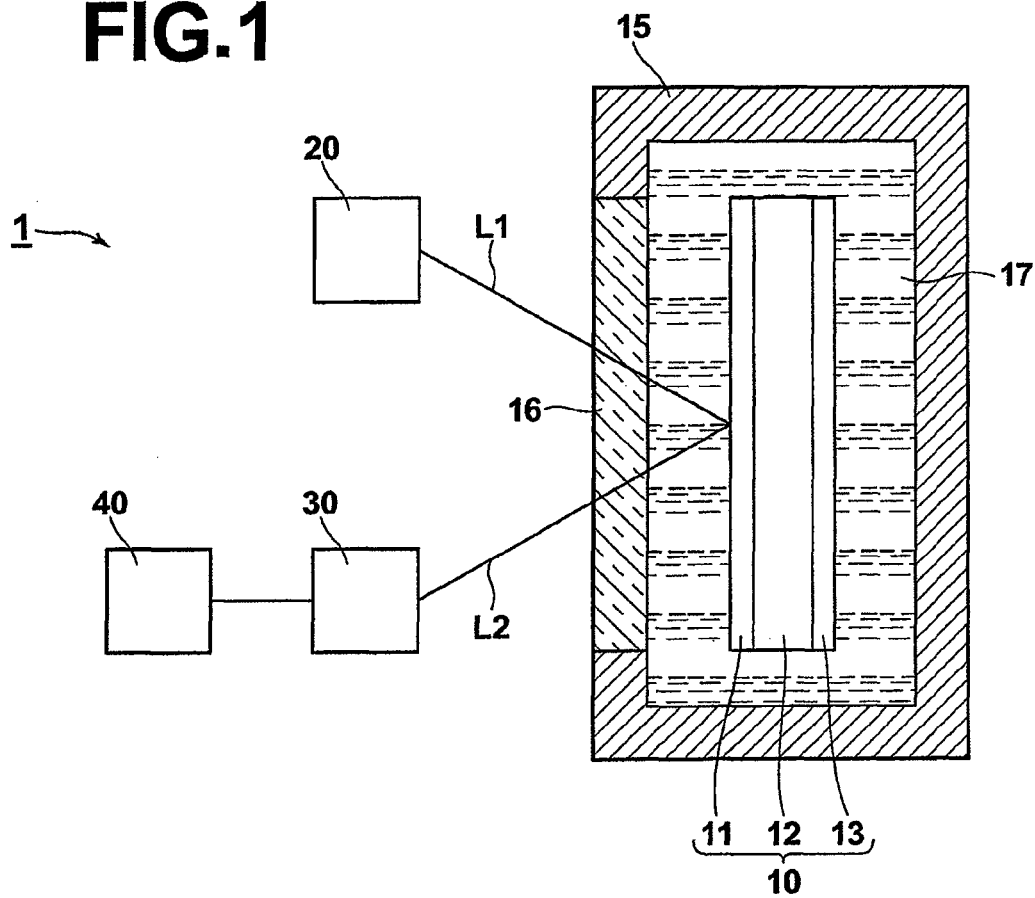

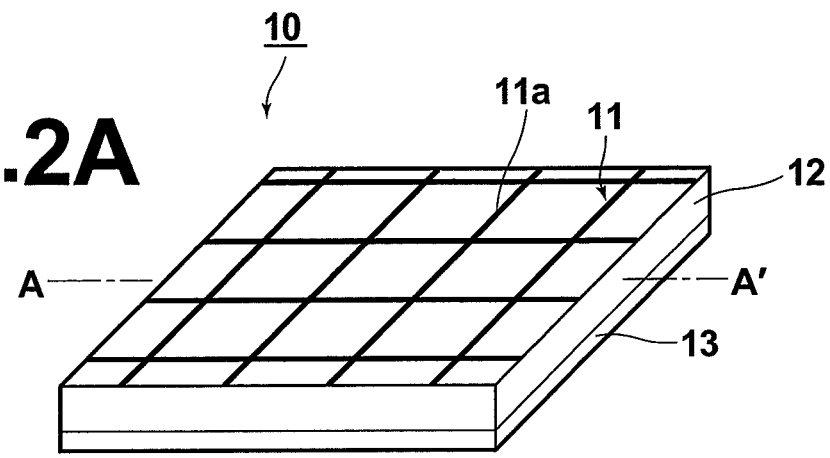
FIG.2A
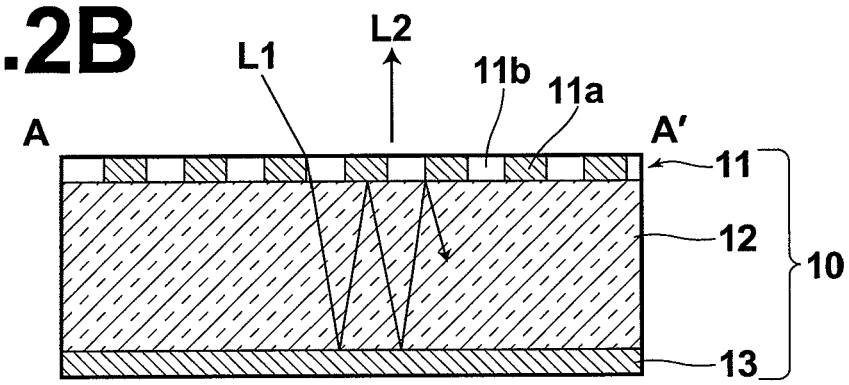
FIG.2B
FIG.2C
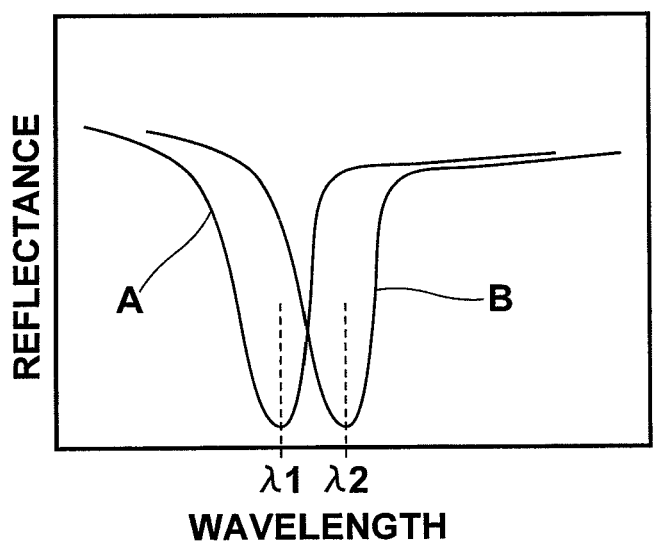

SENSING SYSTEM

TECHNICAL FIELD

The present invention relates to a sensing system for analyzing a specimen by use of a sensing element, and detecting light outputted from the sensing element in response to injection of light for measurement, where the light outputted from the sensing element has a physical characteristic which varies with a specimen.

BACKGROUND ART

Conventionally, sensors utilizing the phenomenon in which the surface plasmon resonance decreases the intensity of reflected light having a specific wavelength have been proposed for use in analysis of biomolecules and the like, and for example, a surface plasmon sensor having as essential constituents a prismatic dielectric block and a metal film which is formed on the dielectric block and is to be arranged in contact with a specimen has been disclosed in, for example, Japanese Unexamined Patent Publication No. 6 (1994)-167443. In such a surface plasmon sensor, a total reflection condition is satisfied at the interface between the dielectric block and the metal film. It is possible to perform measurement of the refractive index or concentration of a specimen, identification of the specimen, and the like by applying light for measurement to the surface plasmon sensor so that surface plasmon resonance causes attenuated total reflection, measuring the intensity of light totally reflected at the interface, and detecting the attenuated total reflection.

However, since the above surface plasmon sensor uses the prismatic dielectric block, the cost of the surface plasmon sensor is high, and the surface plasmon sensor has severe structural constraints on downsizing or adaptation to concurrent analysis of a number of specimens. In order to solve this problem, a sensor which utilizes a phenomenon in which localized plasmon resonance attenuates the intensity of reflected light at a specific wavelength has been proposed, and a local plasmon sensor in which a metal structure is formed with fine protrusions and recesses at a surface of a substrate so that localized plasmon resonance is effectively excited has also been proposed. See Japanese Unexamined Patent Publication No. 2004-232027, and T. Okamoto et al., "Local plasmon sensor with gold colloid monolayers deposited upon glass substrates," Optics Letters, Vol. 25, Issue 6, pp. 372-374 (2000).

Since the above local plasmon sensor does not need the prismatic dielectric block, the local plasmon sensor can be more simply constructed at lower cost than the surface plasmon sensor, and the local plasmon sensor has weaker structural constraints than the surface plasmon sensor. However, the detection sensitivity of the local plasmon sensor is poor compared with the surface plasmon sensor, so that it is difficult to perform high-precision analysis by using the local plasmon sensor.

DISCLOSURE OF THE INVENTION

The object of the present invention is to provide a sensing system which uses a sensing element having satisfactory detection sensitivity and a simpler construction than surface plasmon sensors.

In order to accomplish the above object, the first aspect of the present invention is provided. According to the first aspect of the present invention, there is provided a sensing system comprising: a sensing element which outputs light having a physical characteristic varying with a specimen, in response to injection of light onto the sensing element; a light injection unit which injects laser light as first light onto the sensing element, and has a wavelength stabilizing arrangement stabilizing an oscillation wavelength of the laser light by use of a wavelength selector built in the wavelength stabilizing arrangement; and a light detection unit which detects a physical characteristic of second light which is outputted from the sensing element in response to injection of the first light onto the sensing element. The above sensing element includes a transparent body, a first reflector which is partially transparent and partially reflective, and is arranged on a first side of the transparent body from which the first light and the second light are injected, and a second reflector which is completely reflective, or partially transparent and partially reflective, and is arranged on a second side of the transparent body opposite to the first side. In addition, at least one of the first reflector and the second reflector is arranged in contact with the specimen, and has an average complex refractive index which varies with the specimen; and the sensing element exhibits an absorption characteristic that light injected onto the sensing element is selectively absorbed at a specific wavelength according to average complex refractive indexes which the first reflector and the second reflector respectively have and an average complex refractive index and a thickness which the transparent body has, and outputs light in which the absorption characteristic is reflected, from at least one of the first reflector and the second reflector.

In order to accomplish the aforementioned object, the second aspect of the present invention is also provided. According to the second aspect of the present invention, there is provided a sensing system comprising: a sensing element which outputs light having a physical characteristic varying with a specimen, in response to injection of light onto the sensing element; a light injection unit which injects light with two or more wavelengths onto the sensing element, where the light injected by the light injection unit includes first light having a first wavelength and second light having a second wavelength different from the first wavelength; a light detection unit which detects a first intensity of third light which is outputted from the sensing element in response to injection of the first light onto the sensing element, and a second intensity of fourth light which is outputted from the sensing element in response to injection of the third light onto the sensing element; and a calculation unit which obtains a difference between the first intensity and the second intensity. The above sensing element includes a transparent body, a first reflector which is partially transparent and partially reflective, and is arranged on a first side of the transparent body from which the first light and the second light are injected, and a second reflector which is completely reflective, or partially transparent and partially reflective, and is arranged on a second side of the transparent body opposite to the first side. In addition, at least one of the first reflector and the second reflector is arranged in contact with the specimen, and has an average complex refractive index which varies with the specimen; and the sensing element exhibits an absorption characteristic that light injected onto the sensing element is selectively absorbed at a specific wavelength according to average complex refractive indexes which the first reflector and the second reflector respectively have and an average complex refractive index and a thickness which the transparent body has, and outputs light in which the absorption characteristic is reflected, from at least one of the first reflector and the second reflector.

In this specification, the expression "partially transparent and partially reflective" means to exhibit both of the transparency and reflectiveness although the degrees of the transparency and reflectiveness are not specified.

Preferably, the sensing systems according to the first and second aspects of the present invention may have one or any possible combination of the following additional features (a) to (d).

(a) One or each of the first and second reflectors may have a structure with protrusions and recesses which are finer than the wavelength or wavelengths of the light injected onto the sensing element. The expression "a structure with protrusions and recesses which are finer than the wavelength or wavelengths of the light" means a structure in which the average of the dimensions and the pitches of the protrusions and recesses (in the directions parallel to the upper or lower surface of the sensing element) is smaller than the wavelength or wavelengths of the light, where the recesses may be holes or gaps extending through the entire thickness of the sensing element.

(b) One or each of the first and second reflectors may be a metal layer formed of metal arranged in a pattern on a surface of the transparent body.

(c) One or each of the first and second reflectors may be a metal layer formed of a plurality of metal particles arranged on and fixed to a surface of the transparent body.

(d) The transparent body may be a transparent microporous body having a plurality of micropores which are open on the first-reflector side and have diameters smaller than the wavelength or wavelengths of the light injected onto the sensing element, and the first reflector may be a metal layer having a plurality of micropores which are formed in correspondence with the plurality of micropores open on the first-reflector side, and have an average complex refractive index which varies with the specimen arranged in contact with the at least one of the first reflector and the second reflector.

Further, the sensing system according to the first aspect of the present invention may have one or any possible combination of the following additional features (e) to (h).

(e) The light injected onto the sensing element is laser light, and the injection unit uses a semiconductor laser for reducing the size and weight of the sensing system. In addition, the wavelength stabilizing arrangement may be constituted by a wavelength selector and an optical feedback system which feeds back to the semiconductor laser a portion of a laser beam emitted from the semiconductor laser, where the wavelength selector (wavelength selection means) selects a wavelength of the laser beam fed back to the semiconductor laser, and may be realized by a grating or a band-pass filter.

Specifically, in the case where the above wavelength selector is realized by a bulk grating, the above optical feedback system and wavelength selector can be realized in one of the following manners (i) to (iii).

(i) The above optical feedback system is constituted by an optical splitter and a reflective grating, where the optical splitter is arranged in an optical path of the laser beam emitted from the semiconductor laser and directed toward the sensing element and splits off a portion of the laser beam, and the reflective grating reflects a portion of the laser beam having the selected wavelength so that the portion of the laser beam having the selected wavelength retraces the optical path of the split-off portion of the laser beam. At this time, the reflective grating also has the function of the wavelength selector.

(ii) The above optical feedback system and the wavelength selector may be realized by a partially-reflective grating which is arranged in an optical path of the laser beam emitted from the semiconductor laser toward the dielectric block, and reflects a portion of the laser beam having the selected wavelength so that the partially reflected portion of the laser beam is fed back to the semiconductor laser.

(iii) The optical feedback system and the wavelength selector may be realized by a reflective grating which reflects a portion of backward emission light having the selected wavelength so that the reflected portion of the backward emission light is fed back to the semiconductor laser, where the backward emission light is emitted from the semiconductor laser in the direction opposite to the direction of the laser beam incident on the sensing element.

Alternatively, in the case where the wavelength stabilizing arrangement is constituted by the wavelength selector and the optical feedback system, and the wavelength selector is realized by a narrow-band-pass filter, the optical feedback system and wavelength selector can be realized in one of the following manners (iv) to (vi).

(iv) The aforementioned optical feedback system may be constituted by an optical splitter and a mirror. The optical splitter is arranged in an optical path of the laser beam emitted from the semiconductor laser toward the sensing element, and splits off a portion of the laser beam from the optical path. The mirror reflects the split-off portion of the laser beam so that the reflected portion of the laser beam retraces the path of the split-off portion of the laser beam, and is fed back to the semiconductor laser. The narrow-band-pass filter as the wavelength selector is arranged between the optical splitter and the mirror so that only a component of the split-off portion of the laser beam having a wavelength selected by the narrow-band-pass filter is fed back to the semiconductor laser.

(v) The optical feedback system may be realized by a half mirror, which is arranged in an optical path of the laser beam emitted from the semiconductor laser toward the sensing element, partially reflects the laser beam, and feeds back a portion of the laser beam to the semiconductor laser. The narrow-band-pass filter is arranged in the optical path between the semiconductor laser and the half mirror so that only a portion of the laser beam having a wavelength selected by the narrow-band-pass filter is fed back to the semiconductor laser.

(vi) The optical feedback system may be realized by a mirror, which reflects a portion of backward emission light, and feeds back the backward emission light to the semiconductor laser, where the backward emission light is emitted from the semiconductor laser in the direction opposite to the direction of the laser beam incident on the sensing element. The narrow-band-pass filter is arranged in the optical path between the semiconductor laser and the mirror so that only a portion of the backward emission light having a wavelength selected by the narrow-band-pass filter is fed back to the semiconductor laser.

Further alternatively, in the case where the wavelength stabilizing arrangement is constituted by the wavelength selector and the optical feedback system, the wavelength selector may be realized by using a fiber grating, which diffracts and reflects the laser beam. The fiber grating is an optical fiber having a core in which a plurality of refractive-index-varied portions are formed at regular intervals. In this case, the optical feedback system can be realized in one of the following manners (vii) to (ix).

(vii) The optical feedback system may be constituted by an optical splitter and the fiber grating, which realizes the wavelength selector. The optical splitter is arranged in an optical path of the laser beam emitted from the semiconductor laser toward the sensing element, and splits off a portion of the laser beam from the optical path. The fiber grating diffracts and reflects a component of the split-off portion of the laser beam having the selected wavelength so that the reflected component of the split-off portion of the laser beam retraces the path of the split-off portion of the laser beam, and is fed back to the semiconductor laser.

(viii) The optical feedback system and the wavelength selector may be realized by a partially-reflective fiber grating which is arranged in an optical path of the laser beam emitted from the semiconductor laser toward the sensing element, and partially reflects a portion of the laser beam having the selected wavelength so that the partially reflected portion of the laser beam is fed back to the semiconductor laser.

(ix) The optical feedback system and the wavelength selector may be realized by the fiber grating which reflects a portion of backward emission light having the selected wavelength so that the reflected portion of the backward emission light is fed back to the semiconductor laser.

(f) It is also possible to stabilize the oscillation wavelength by using a semiconductor laser in which a wavelength stabilization unit is built in, such as a DFB (distributed feedback) laser or DBR (distributed Bragg reflector) laser. In this case, the oscillation wavelength can be stabilized without using the aforementioned optical feedback system.

(g) Alternatively, it is possible to stabilize the oscillation wavelength by electrically and finely controlling the temperature and the driving current of the semiconductor laser.

(h) The light detection unit detects at least one of the intensity of the light outputted from the sensing element, the variation in the intensity the light outputted from the sensing element, the absorption wavelength (i.e., the wavelength of light absorbed by the sensing element), or the shift in the absorption wavelength.

Furthermore, the sensing system according to the second aspect of the present invention may have one or any possible combination of the following additional features (j) and (k).

(j) It is preferable that the light injection unit have two (or more) light sources emitting light beams for measurement having two (or more) different wavelengths, and be arranged to optically combine the light beams for measurement having the two (or more) different wavelengths into a single light beam and lead the combined light beam to the sensing element. In addition, it is also preferable that the light detection unit be constituted by an optical splitting unit and a plurality of optical detectors. The optical splitting unit splits the light outputted from the sensing element, into components having the two (or more) different wavelengths, and the plurality of optical detectors respectively detect the intensities of the respective components at the two (or more) different wavelengths outputted from the sensing element.

(k) Alternatively, it is also preferable that the light injection unit be arranged to inject two (or more) first light beams having two (or more) wavelength at time intervals, and the light detection unit be realized by a single optical detector which operates in synchronization with the injection of the two (or more) first light beams so as to detect the intensities of two (or more) second light beams having the two (or more) wavelengths outputted from the sensing element in correspondence with the two (or more) first light beams. In this case, it is possible to fix at different positions two (or more) light sources which respectively emit the two (or more) first light beams, and lead the two (or more) first light beams to an identical optical path, for example, by using a dichroic mirror.

Since the two (or more) light sources emit the two (or more) first light beams at time intervals, the two (or more) first light beams are not optically combined. Alternatively, it is possible to move the above two (or more) light sources so that each of the two (or more) light sources is located at an identical position with respect to the position of the sensing element when the light source is activated. Further alternatively, it is possible to combine a wavelength selector and a single light source which can emit light at a plurality of wavelengths, so as to inject the two (or more) first light beams at time intervals. Even in these cases, the light detection unit may be constituted by the optical splitting unit and the plurality of optical detectors as indicated in the paragraph (j).

The sensing systems according to the first and second aspects of the present invention have the following advantages.

In the sensing systems according to the first and second aspects of the present invention, the sensing element is constituted by the first reflector, the transparent body, and the second reflector formed in this order from the light-injection side. Therefore, when the light is injected onto the sensing element, the light passes through the first reflector, enters the transparent body, and is repeatedly reflected between the first and second reflectors. That is, multiple reflection (resonance) effectively occurs, so that the multiply reflected light effectively causes multiple interference. Since the condition for multiple interference varies with the factors of the thickness of the transparent body 12 and the average complex refractive indexes of the first reflector, the transparent body, and the second reflector, the sensing element exhibits an absorption characteristic of absorbing light at a specific wavelength according to the above factors, and outputs through the first or second reflector light having a physical characteristic which is different from the physical characteristic of the light injected onto the sensing element and depends on the above absorption characteristic. When at least one of the first and second reflectors is arranged in contact with a specimen, the average complex refractive index of the at least one of the first and second reflectors varies with the specimen, so that the condition for multiple interference and the absorption characteristic also vary. Therefore, it is possible to perform analysis of the specimen by detecting the physical characteristic of the light outputted from the sensing element, which varies with the absorption characteristic.

Since the sensing element used in the first or second aspect of the present invention has a device structure in which the transparent body is sandwiched between two types of reflectors, the device structure of the sensing element is very simple, the structural constraints imposed on the sensing element are weak, and the cost of the sensing element is low, compared with the conventional surface plasmon sensors. In addition, since the multiple interference effectively occurs and strong light absorption occurs at the specific wavelength, the sensing element enables achievement of higher detection sensitivity than the conventional localized plasmon sensors, and high-precision analysis of the specimen.

When measurement is performed by using the above sensing element, the measurement result can sensitively vary with the variations in the wavelength of the light injected onto the sensing element for the measurement, so that the precision in the measurement can be lowered. However, in the sensing system according to the first aspect of the present invention, the light injection unit includes a wavelength stabilizing arrangement in which a wavelength selector is built in, and which stabilizes an oscillation wavelength of laser light, and the light injection unit injects the laser light (as the first light) onto the sensing element. Therefore, it is possible to suppress the variations in the oscillation wavelength of the (first) light injected onto the sensing element, and thus achieve measurement with sufficiently high precision.

Further, when measurement is performed by using the above sensing element, noise components can be superimposed on the outputs of the light detection unit indicating the intensities of the light outputted from the sensing element in response to injection of light, so that the signal-to-noise ratios in the detected intensities can be lowered. However, this problem is overcome in the sensing system according to the second aspect of the present invention as explained below.

FIG. 2C shows spectra of light which is outputted from an example of the sensing element used in the sensing system according to the first or second aspect of the present invention when the first reflector is arranged in contact with different specimens A and B and white light is injected onto the sensing element. FIG. 2C shows that when the specimen is changed from A to B, the absorption peak wavelength is also changed from λ1 to λ2. That is, the absorption peak wavelength of the sensing element varies with the specimen. Therefore, the difference between the detected intensities of the light outputted from the sensing element at two different wavelengths also varies with the specimen, so that it is possible to perform quantitative analysis of specimens on the basis of the difference.

The sensing system according to the second aspect of the present invention utilizes the above fact. That is, two or more light beams (including the first light and the second light) having two or more wavelengths are injected onto the sensing element by the light injection unit, and the intensities of light outputted from the sensing element at the two wavelengths are detected by the light detection unit. Further, the difference between the detected intensities of light at the two wavelengths is obtained by the calculation unit. Therefore, it is possible to cancel out the noise components superimposed on the outputs of the light detection unit indicating the intensities of the light outputted from the sensing element at the two wavelengths (the third light and the fourth light), and achieve measurement with sufficiently high precision.

BRIEF DESCRIPTION OF THE DRAWINGS

FIG. 1 is a plan view of a sensing system according to a first embodiment of the present invention.

FIG. 2A is a perspective view of a sensing element used in the sensing system of FIG. 1.

FIG. 2B is a cross-sectional view of the sensing element of FIG. 2A at the A-A' cross section indicated in FIG. 2A.

FIG. 2C is a graph indicating spectra of light outputted from the sensing element of FIGS. 2A and 2B.

BEST MODE FOR CARRYING OUT THE INVENTION

Figure 3:
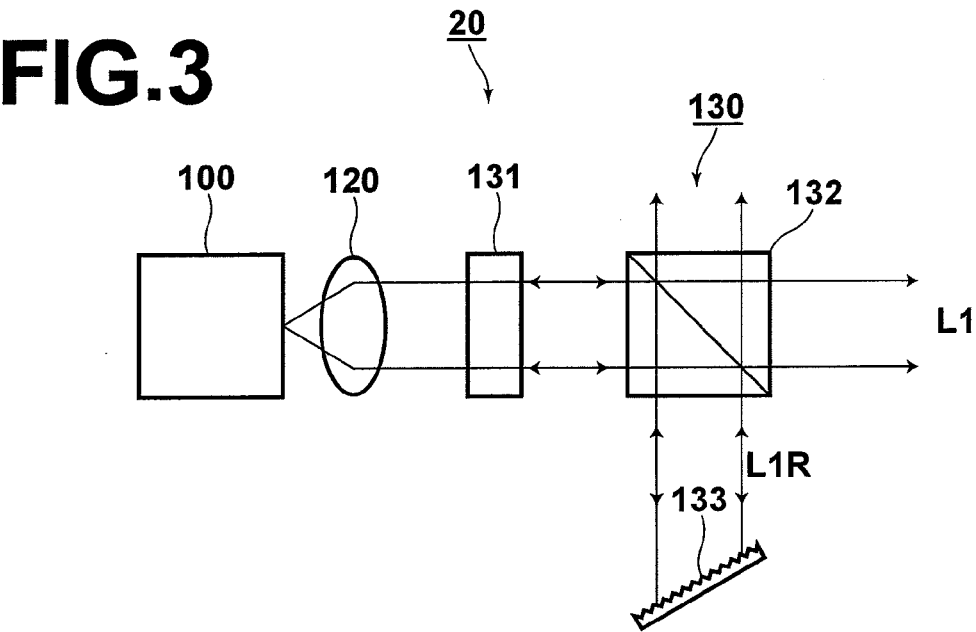
FIG. 3 is a schematic diagram illustrating a light injection unit in the sensing system of FIG. 1.

Preferred embodiments of the present invention are explained in detail below with reference to drawings. In the drawings, equivalent elements and constituents are indicated by the same reference numbers even in drawings for different embodiments, and descriptions of the equivalent elements or constituents are not repeated in the following explanations unless necessary.

First Embodiment

FIG. 1 is a plan view of a sensing system 1 according to a first embodiment of the present invention. The sensing system 1 comprises a sensing element 10, a specimen cell 15, a light injection unit 20, a light detection unit 30, and a data processing unit 40.

When light L1 for measurement (hereinafter referred to as measurement light L1) is injected onto the sensing element 10, the sensing element 10 outputs output light L2 having a physical characteristic which depends on a specimen 17. The specimen cell 15 contains the sensing element 10 and the specimen 17, and the light injection unit 20 injects the measurement light L1 onto the sensing element 10. The light detection unit 30 detects the physical characteristic of the output light L2, and outputs a signal representing the detection result. The data processing unit 40 performs analysis of the specimen 17 on the basis of the signal outputted from the light detection unit 30.

First, the sensing element 10 is explained below.

FIG. 2A is a perspective view of a sensing element used in the sensing system of FIG. 1, and FIG. 2B is a cross-sectional view of the sensing element of FIG. 2A at the A-A' cross section indicated in FIG. 2A. As illustrated in FIG. 2A, the sensing element 10 has a structure constituted by a first reflector 11, a transparent body 12, and a second reflector 13. The first reflector 11 is arranged on the light-injection side (the upper side in FIG. 2A) of the transparent body 12, and the second reflector 13 is arranged on the opposite side of the transparent body 12. The first reflector 11 is partially transparent and partially reflective, and the second reflector 13 is completely reflective.

The transparent body 12 is realized by a planar transparent substrate. The first reflector 11 is realized by arranging fine metal wires 11a on a first surface of the transparent body 12 in a regular grid pattern, and the second reflector 13 is realized by a metal layer formed all over a second surface of the transparent body 12 which is opposite to the first surface.

The material of which the transparent body 12 is made is not specifically limited. For example, the transparent body 12 may be made of a transparent ceramic material (such as glass or alumina), a transparent resin (such as acrylic resin or carbonate resin), or the like. The metal wires 11a and the second reflector 13 may be made of a reflective metal, for example, Au, Ag, Cu, Al, Pt, Ni, Ti, or an alloy of two or more of these reflective metals. Alternatively, the metal wires 11a and the second reflector 13 may be made of two or more types of reflective metals.

The second reflector 13 may be formed, for example, by evaporation. The grid pattern of the metal wires 11a can be realized, for example, by forming a metal layer all over the first surface, and then forming the grid pattern by well-known photolithography.

Although the metal wires 11a constituting the first reflector 11 are formed of reflective metal, a plurality of spaces (gaps) 11b exist between the metal wires 11a. Therefore, the first reflector 11 is transparent at the plurality of spaces (gaps) 11b, and the first reflector 11 becomes partially transparent and partially reflective. The width of the metal wires 11a and the pitch of the grid pattern are designed to be smaller than the wavelength of the measurement light L1. That is, the first reflector 11 has a structure with projections and recesses finer than the wavelength of the measurement light L1. In this case, since the wire mesh has the electromagnetic shield effect, the metal wires 11a formed in the grid pattern behave as a thin film which is partially transparent and partially reflective.

The average complex refractive indexes of the first reflector 11 and the second reflector 13 vary with the specimen which is in contact with the first reflector 11 and the second reflector 13. Therefore, it is possible to perform analysis of the specimen by arranging the sensing element 10 so that the first reflector 11 and the second reflector 13 are in contact with the specimen.

In particular, since the first reflector 11 has the structure with the protrusions and recesses finer than the wavelength of the measurement light L1, the average complex refractive index particularly sensitively varies with the specimen. It is possible to consider that the structure of the first reflector 11 having the protrusions and recesses finer than the wavelength of the measurement light L1 makes the oscillation by the measurement light L1 more effective. Therefore, it is preferable to perform the analysis by arranging the specimen in contact with at least the first reflector 11.

It is sufficient that the pitch of the grid pattern of the metal wires 11a is smaller than the wavelength of the measurement light L1. For example, when the measurement light L1 is visible light, it is preferable that the pitch of the grid pattern of the metal wires 11a be 200 nm or smaller. However, from the viewpoint of the sensitivity, it is more preferable that the grid pattern of the metal wires 11a have a smaller pitch.

Although it is also sufficient that the width of the metal wires 11a is smaller than the wavelength of the measurement light L1, from the viewpoint of the sensitivity, it is more preferable that the metal wires 11a have a smaller width.

Further, it is preferable that the width of the metal wires 11a be equal to or smaller than the mean free path of the electrons which vibrate in the metal by the action of the light. Specifically, the width of the metal wires 11a is preferably equal to or smaller than 50 nm, and more preferably equal to or smaller than 30 nm.

When the pitch of the grid pattern of the metal wires 11a and the width of the metal wires 11a are smaller, the surface area of each of the metal wires 11a is relatively greater, so that the surface characteristics of the metal wires 11a are more easily reflected in the overall characteristics of the first reflector 11, and higher sensitivity can be achieved. Specifically, when the pitch of the grid pattern of the metal wires 11a and the width of the metal wires 11a are smaller, the difference between the values of the dielectric constant (permittivity) of the first reflector 11 detected with the different specimens is greater, so that the difference between the values of the average complex refractive index of the first reflector 11 detected with the different specimens is greater, and higher sensitivity can be achieved.

As illustrated in FIG. 2B, when the measurement light L1 is injected onto the sensing element 10, a first portion of the measurement light L1 is reflected at the surface of the first reflector 11 (although not shown), and a second portion passes through the first reflector 11 and enters the transparent body 12, where the first and second portions are determined according to the transmittance and reflectance of the first reflector 11. Then, the second portion of the measurement light L1 is repeatedly reflected by the first reflector 11 and the second reflector 13. That is, the sensing element 10 has a resonance structure which causes multiple reflection between the first reflector 11 and the second reflector 13.

In the above sensing element 10, the multiply reflected light causes multiple interference, so that the sensing element 10 exhibits an absorption characteristic that light at a specific wavelength is selectively absorbed. The condition for multiple interference varies with the thickness of the transparent body 12 and the average complex refractive indexes of the first reflector 11, transparent body 12, and the second reflector 13. Therefore, the specific wavelength in the above absorption characteristic depends on the the thickness of the transparent body 12 and the average complex refractive indexes of the first reflector 11, transparent body 12, and the second reflector 13. In addition, the sensing element 10 outputs output light L2 having a physical characteristic which is different from the physical characteristic of the measurement light L1 and depends on the above absorption characteristic. Since the second reflector 13 is completely reflective in this embodiment, the output light L2 is outputted from only the first reflector 11.

The peak wavelength $\lambda$ of the light absorbed by the multiple interference is expressed as $$\lambda = 4\pi n_2 d/(2\pi - \phi 1 - \phi 2),$$

where the phase shift which occurs when light is reflected by the first reflector 11 is expressed as $\phi 1$, and the phase shift which occurs when light is reflected by the second reflector 13 is expressed as $\phi 2$. The phase shifts $\phi 1$ and $\phi 2$ are respectively expressed as $$\phi 1 = \tan^{-1}[2n_2 k_1/(n_2^2 - n_1^2 - k_1^2)], \text{ and}$$

$$\phi 2 = \tan^{-1}[2n_2 k_3/(n_2^2 - n_3^2 - k_3^2)],$$

where the average complex refractive index of the first reflector 11 is expressed as $n_1 - ik_1$, the average complex refractive index of the transparent body 12 is expressed as $n_2$, the average complex refractive index of the second reflector 13 is expressed as $n_3-ik_3$, and the thickness of the transparent body 12 is expressed as d. At this time, i is the imaginary unit. In this embodiment, the imaginary part of the average complex refractive index of the transparent body 12 is zero.

In particular, in the case where at least one of the first reflector 11, the transparent body 12, and the second reflector 13 is formed of a light absorbing material the complex refractive index of which has a non-zero imaginary part, the absorption peak becomes sharp, i.e., the sensing element 10 exhibits strong light absorption at a specific wavelength. As indicated above, in this embodiment, the first reflector 11 and the second reflector 13 are formed of light absorbing materials which have a non-zero imaginary part of the complex refractive index.

There is no specific limit to the thickness d of the transparent body 12. However, it is preferable that the thickness of the transparent body 12 be 300 nm or smaller. This is because in the case where the thickness of the transparent body 12 is 300 nm or smaller, only one absorption peak is produced in the visible-light wavelength range by the multiple interference, and the absorption peak can be easily detected. In addition, it is also preferable that the thickness of the transparent body 12 be 100 nm or greater. This is because in the case where the thickness of the transparent body 12 is 100 nm or greater, the multiple interference effectively occurs, and the absorption peak produced by the multiple interference belongs to the visible-light wavelength range, so that the absorption peak can be easily detected.

Further, it is preferable that the sensing element 10 have a device structure in which the optical impedance is matched, so that the number of the multiple reflections in the transparent body 12 is maximized (i.e., the finesses is maximized). In this case, the absorption peak becomes sharp, and high-precision analysis can be performed.

When one or both of the first reflector 11 and the second reflector 13 are (preferably only the first reflector 11 is) arranged in contact with the specimen, the average (effective) complex refractive index or indexes of the reflector or reflectors which are arranged in contact with the specimen are changed by interaction between the specimen and the reflector or reflectors, and therefore the condition for multiple interference is changed. That is, the absorption characteristic produced by the multiple interference varies with the specimen.

Examples of spectra of reflected light which is outputted from the sensing element 10 when the first reflector 11 is arranged in contact with the specimen A or B and white light as the measurement light L1 is injected onto the first reflector 11 are indicated in FIG. 2C. FIG. 2C shows that when the specimen is changed, the absorption peak wavelength is changed from $\lambda 1$ to $\lambda 2$.

The specimen can be analyzed by detecting the physical characteristic of the output light L2 from the sensing element 10, since the physical characteristic of the output light L2 varies with the absorption characteristic of the sensing element 10. The physical characteristic of the output light L2 may be, for example, the intensity of the output light L2, the variation in the intensity of the output light L2, the absorption wavelength (i.e., the wavelength of light absorbed by the sensing element 10), or the shift in the absorption wavelength.

When the above sensing element 10 is used, it is possible to analyze the refractive index and/or concentration of the specimen, and identify the specimen by analyzing the refractive index of the specimen. In addition, it is also possible to determine presence or absence of a specific material in the specimen, or analyze the quantity of the specific material contained in the specimen, by fixing a specific binding material (which can be specifically bound to the specific material) to the reflector or reflectors (one or both of the first reflector 11 and the second reflector 13) which are to be arranged in contact with the specimen, arranging the reflector or reflectors in contact with the specimen, injecting the measurement light L1 onto the sensing element 10, and detecting the output light L2 outputted from the sensing element 10. For example, the specific material and the specific binding material may be an antigen and an antibody, where either of the antigen and the antibody can be the specific material. Furthermore, it is possible to perform time-series analysis of antigen-antibody reaction and the like.

As explained above, in the sensing element 10 used in the first embodiment, the first reflector 11, the transparent body 12, and the second reflector 13 are arranged in this order from the light-injection side. Therefore, the measurement light L1 injected into the transparent body 12 through the first reflector 11 is repeatedly reflected between the first reflector 11 and the second reflector 13. That is, multiple reflection (resonance) effectively occur, and the multiply reflected light effectively causes multiple interference. Since the condition for the multiple interference varies with the factors of the thickness of the transparent body 12 and the average complex refractive indexes of the first reflector 11, the transparent body 12, and the second reflector 13, the sensing element 10 has an absorption characteristic that light having a specific wavelength according to the above factors is absorbed, and the output light L2 having a physical characteristic which is different from the physical characteristic of the measurement light L1 and in which the absorption characteristic of the sensing element 10 is reflected is outputted from the first reflector 11. In addition, when one or both of the first reflector 11 and the second reflector 13 are arranged in contact with the specimen, the average complex refractive index or indexes of the one or both of the first reflector 11 and the second reflector 13 vary with the specimen. Since the condition for the multiple interference and the absorption characteristic of the sensing element 10 vary with the specimen in contact with the one or both of the first reflector 11 and the second reflector 13, the physical characteristic of the output light L2 outputted from the sensing element 10 also varies with the specimen. Therefore, it is possible to perform analysis of the specimen by detecting the physical characteristic of the output light L2.

Since the sensing element 10 used in the first embodiment has a device structure in which the transparent body 12 is sandwiched between two types of reflectors 11 and 13, the device structure of the sensing element 10 is very simple, the structural constraints imposed on the sensing element 10 are weak, and the cost of the sensing element 10 is low, compared with the conventional surface plasmon sensors. In addition, since the multiple interference effectively occurs and strong light absorption occurs at the specific wavelength, the sensing element 10 can achieve higher detection sensitivity than the conventional localized plasmon sensors, and enables high-precision analysis of the specimen.

Further, since the first reflector 11 and the second reflector 13 constituting the sensing element 10 used in the first embodiment are formed of metals having free electrons, it is possible to excite localized plasmon resonance at the surfaces of the first reflector 11 and the second reflector 13.

The localized plasmon resonance is a phenomenon in which free electrons in metal oscillate in resonance with the electric field of light. In particular, in a metal layer having a structure with protrusions and recesses, oscillation of free electrons at the protrusions in resonance with the electric field of light produces a strong electric field in the vicinities of the protrusions, and effectively excites localized plasmon resonance. According to the first embodiment, the first reflector 11 in the sensing element 10 realizes a structure with the protrusions and recesses finer than the wavelength of the measurement light L1. Therefore, the localized plasmon resonance is effectively excited.

Scattering and absorption of the measurement light L1 is greatly enhanced at the wavelength at which the localized plasmon resonance occurs (i.e., the resonance peak wavelength), so that the intensity of the reflected light at the wavelength is greatly attenuated. The resonance peak wavelength and the degrees of the scattering and the absorption of the measurement light L1 depend on the refractive index and the like of the specimen which is arranged in contact with the surface of the sensing element 10.

Since the absorption peak wavelength and the resonance peak wavelength are normally different, it is possible to perform analysis of the specimen with further higher precision by detecting variations in the physical characteristic caused by each of the multiple interference and the localized plasmon resonance in the sensing element 10, although the resonance peak wavelength is not indicated in FIG. 2C. However, in some cases, the absorption peak wavelength and the resonance peak wavelength may overlap.

From the viewpoint of the capability of sensing based on the localized plasmon resonance, it is preferable that the first reflector 11 and the second reflector 13 be formed of metal. However, it is possible to form the first reflector 11 and/or the second reflector 13 of a reflective material other than metals.

Although the first reflector 11 is formed by arranging the metal wires 11a in the regular grid pattern in the sensing element 10, alternatively, it is possible to form the first reflector 11 in an arbitrary pattern, for example, a random pattern. However, when the structural regularity of the first reflector 11 is high, the uniformity of the resonance structure over the entire surface is high, so that the characteristic of the resonance structure is intensified. Therefore, from the viewpoint of the sensitivity, it is preferable that the first reflector 11 have high structural regularity.

The specimen cell 15 contains the sensing element 10 and the specimen 17, and the sensing element 10 is permanently or detachably fixed in the specimen cell 15 by using a fixing structure (not shown) so that the first reflector 11 and the second reflector 13 are in contact with the specimen 17.

As illustrated in FIG. 1, the specimen cell 15 is constituted by a cell body and a transparent window 16. The cell body is formed of a nontransparent material such as metal in such a shape that the specimen cell 15 has a window and can be filled with the specimen 17, and the transparent window panel 16 is transparent to the measurement light L1 and the output light L2 and inserted into the window of the cell body. The window panel 16 and the sensing element 10 are arranged so that the first reflector 11 faces the window panel 16.

FIG. 3 is a schematic diagram illustrating the light injection unit 20 in the sensing system of FIG. 1. The light injection unit 20 comprises a semiconductor laser 100, a collimator lens 120, and a wavelength stabilizing arrangement 130. The semiconductor laser 100 emits a light beam as the measurement light L1, and the collimator lens 120 collimates the light beam L1. The wavelength stabilizing arrangement 130 is constituted by a half-wavelength plate 131, a beam splitter 132, and a reflective grating 133. The half-wavelength plate 131 controls the polarization of the light beam L1. The beam splitter 132 partially reflects the light beam L1 so that a portion L1R of the light beam L1 (hereinafter referred to as the light beam L1R) branches off toward the reflective grating 133. The reflective grating 133 is arranged in the optical path of the reflected light beam L1R. The light beam L1R incident on the reflective grating 133 is reflected toward the beam splitter 132 so that the reflected light beam L1R retraces the optical path of the light beam L1R and is fed back to the semiconductor laser 100 through the beam splitter 132 and the half-wavelength plate 131. When the light beam L1R is reflected by the reflective grating 133, the light beam L1R undergoes wavelength selection so that the spectrum of the light beam L1R is narrowed. Thus, an external resonator is formed between the backward end face of the semiconductor laser 100 and the reflective grating 133, and the oscillation wavelength of the semiconductor laser 100 is locked at the selected wavelength of the reflective grating 133.

The stabilization of the oscillation wavelength of the semiconductor laser 100 as explained above prevents production of noise in measured signals by variations of the oscillation wavelength, and contributes to high-precision in measurement for analysis of the specimen.

The light detection unit 30 is realized by a photodiode, which detects the intensity of the output light L2.

In the sensing system 1 according to the first embodiment, a light-guiding optical system constituted by one or more of collimator lenses, condensing lenses, and the like may be provided with each of the light injection unit 20 and the light detection unit 30 as needed.

In the sensing system 1 having constructed as above, the specimen is analyzed by injecting a single-wavelength light beam (as the measurement light L1) onto the sensing element 10 by the light injection unit 20, and detecting the intensity of the reflected light (as the output light L2) by the light detection unit 30. The measurement light L1 may have an arbitrary wavelength. FIG. 2C also shows that the intensity of the output light L2 at a certain wavelength varies with the specimen. In other words, FIG. 2C shows that analysis of the specimen can be performed by detecting the intensity of the output light L2.

As mentioned before, the sensing system 1 according to the first embodiment can analyze the refractive index and/or concentration of the specimen, and identify the specimen by analyzing the refractive index of the specimen. In addition, the sensing system 1 can determine presence or absence of a specific material in the specimen, or analyze the quantity of the specific material contained in the specimen, by fixing a specific binding material (which can be specifically bound to the specific material) to a surface or surfaces of the sensing element 10 which are to be arranged in contact with the specimen, arranging the surface or surfaces in contact with the specimen, injecting the measurement light L1 onto the sensing element 10, and detecting the output light L2 outputted from the sensing element 10. After the output light L2 is measured as above, it is possible to reuse the sensing element 10 by separating the specific binding material bound to the specific material and the specific binding material fixed to the sensing element 10 in the manners as disclosed in PCT Japanese Publication Nos. 11 (1999)-512518, 2002-517720 and 2003-527606.

In the sensing system 1 according to the first embodiment using the reflective sensing element 10 explained before, it is preferable that the light detection unit 30 detect the output light L2 by receiving only nonregular-reflection components such as scattered light included in the output light L2 outputted from the first reflector 11. Since the intensity of the regular-reflection components of the output light L2 is too high, there is a possibility that the characteristic which is required to be detected cannot be satisfactorily detected on the basis of the intensity of the regular-reflection components. However, in the case where the weak light such as the scattered light is detected, the analysis can be performed with higher precision. In addition, for a similar reason, it is preferable that the light injection unit 20 be arranged at such a position that the light injection unit 20 can inject the measurement light L1 in a direction which is not perpendicular to the incident plane of the sensing element 10.

The construction of the specimen cell 15 used in the sensing system 1 is not limited to the aforementioned construction, and may be arranged in various manners. For example, in the case where a partially-transparent, partially-reflective sensing element or a reflective sensing element which outputs the output light L2 from the first reflector 11 is used, the specimen cell 15 may be arranged so that only the second reflector 13 is in contact with the specimen 17.

In particular, the wavelength stabilizing arrangement 130 may be realized in various manners. The second to tenth embodiments explained below are different from the first embodiment basically only in the wavelength stabilizing arrangement.

Second Embodiment

A sensing system according to the second embodiment of the present invention is explained below with reference to FIG. 4, which is a schematic diagram illustrating a light injection unit 20-1 used in the sensing system according to the second embodiment.

Figure 4:
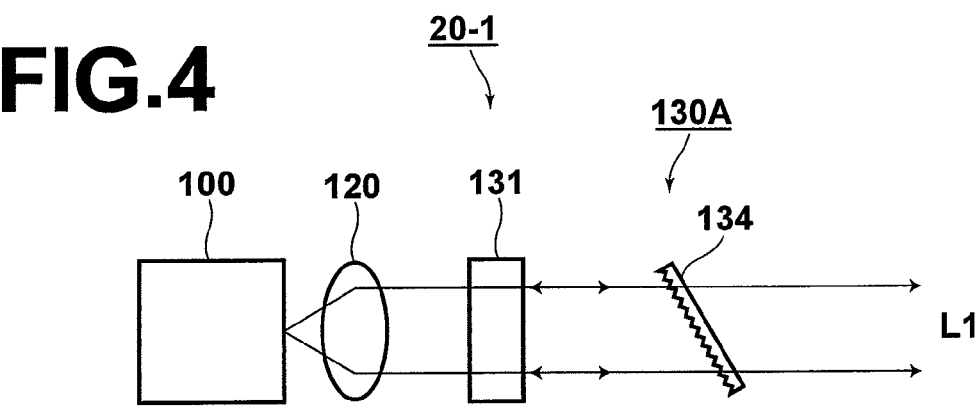
FIG. 4 is a schematic diagram illustrating a light injection unit in a sensing system according to a second embodiment of the present invention.

The light injection unit 20-1 illustrated in FIG. 4 is different from the light injection unit 20 illustrated in FIG. 3 in that the beam splitter 132 and the reflective grating 133 in FIG. 3 are replaced with a partially-reflective grating 134 in FIG. 4. The wavelength stabilizing arrangement 130A in the light injection unit 20-1 is realized by the partially-reflective grating 134. The partially-reflective grating 134 is arranged in the optical path of the measurement light L1 directed to the sensing element 10, and reflects a portion of the measurement light L1. The reflected measurement light L1 is fed back to the semiconductor laser 100 through the half-wavelength plate 131, so that the oscillation wavelength of the semiconductor laser 100 is locked at the selected wavelength of the partially-reflective grating 134.

Third Embodiment

A sensing system according to the third embodiment of the present invention is explained below with reference to FIG. 5, which is a schematic diagram illustrating a light injection unit 20-2 used in the sensing system according to the third embodiment.

Figure 5:
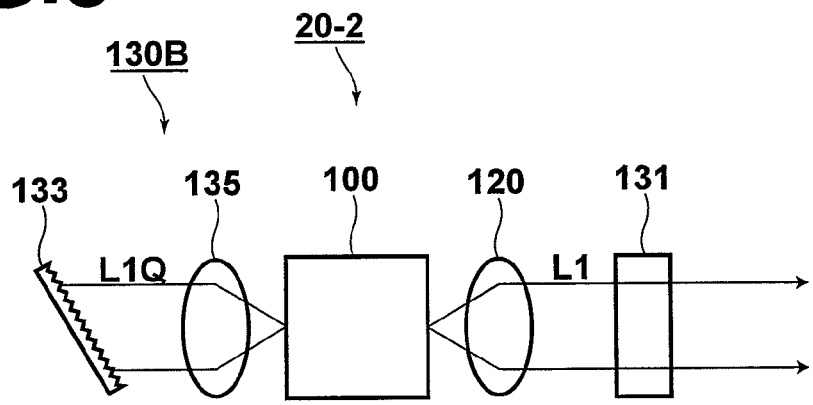
FIG. 5 is a schematic diagram illustrating a light injection unit in a sensing system according to a third embodiment of the present invention.

In the light injection unit 20-2 illustrated in FIG. 5, a reflective grating 133 and a collimator lens 135 are arranged on the backward side of the semiconductor laser 100, and the collimator lens 120 and the half-wavelength plate 131 are arranged on the forward side of the semiconductor laser 100, so that an optical feedback system realizing a wavelength selection arrangement 130B is formed. The wavelength stabilizing arrangement 130B in the light injection unit 20-2 is realized by the reflective grating 133 and the collimator lens 135. That is, the light emitted backward from the semiconductor laser 100 (backward emission light L1Q) is collimated by the collimator lens 135 and is then incident on the reflective grating 133. The backward emission light L1Q is reflected by the reflective grating 133, and fed back to the semiconductor laser 100, so that the oscillation wavelength of the semiconductor laser 100 is locked at the selected wavelength of the reflective grating 133.

Fourth Embodiment

A sensing system according to the fourth embodiment of the present invention is explained below with reference to FIG. 6, which is a schematic diagram illustrating a light injection unit 20-3 used in the sensing system according to the fourth embodiment.

Figure 6:
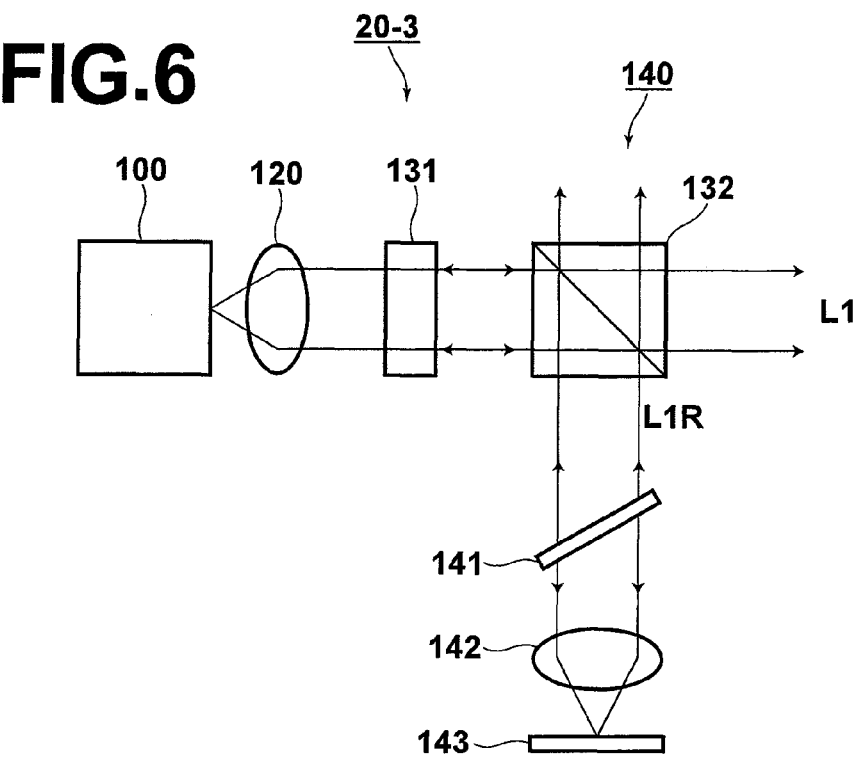
FIG. 6 is a schematic diagram illustrating a light injection unit in a sensing system according to a fourth embodiment of the present invention.

The light injection unit 20-3 illustrated in FIG. 6 is different from the light injection unit 20 illustrated in FIG. 3 in that the reflective grating 133 in FIG. 3 is replaced with a narrow-band-pass filter 141, a condensing lens 142, and a mirror 143 in FIG. 6. The wavelength stabilizing arrangement 140 in the light injection unit 20-3 is realized by the beam splitter 132, the narrow-band-pass filter 141, the condensing lens 142, and the mirror 143. The narrow-band-pass filter 141 is arranged in the optical path of the light beam L1R, which branches off from the measurement light L1 at the beam splitter 132. The light beam L1R undergoes wavelength selection in the narrow-band-pass filter 141 so that the light beam L1R has a very narrow band width after the light beam L1R passes through the narrow-band-pass filter 141. The condensing lens 142 condenses the light beam L1R after the light beam L1R passes through the narrow-band-pass filter 141. The mirror 143 is arranged at the focal position of the condensing lens 142, and reflects the light beam L1R toward the beam splitter 132 so that the reflected light beam L1R retraces the optical path of the light beam L1R and is fed back to the semiconductor laser 100 through the beam splitter 132 and the half-wavelength plate 131. Thus, the oscillation wavelength of the semiconductor laser 100 is locked at the selected wavelength of the narrow-band-pass filter 141, and the light injection unit 20-3 also contributes to high-precision measurement in the sensing system 1.

Fifth Embodiment

A sensing system according to the fifth embodiment of the present invention is explained below with reference to FIG. 7, which is a schematic diagram illustrating a light injection unit 20-4 used in the sensing system according to the fifth embodiment.

Figure 7:
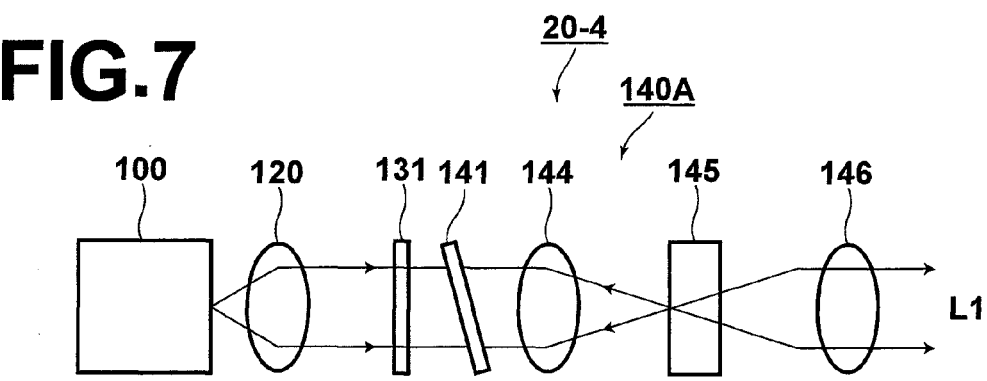
FIG. 7 is a schematic diagram illustrating a light injection unit in a sensing system according to a fifth embodiment of the present invention.

In the light injection unit 20-4 illustrated in FIG. 7 is different from the light injection unit 20-1 illustrated in FIG. 4 in that the partially-reflective grating 134 in FIG. 4 is replaced with a narrow-band-pass filter 141, a condensing lens 144, a half mirror 145, and a collimator lens 146 in FIG. 7, which are arranged in this order in the optical path of the measurement light L1 emitted from the semiconductor laser 100 and directed to the sensing element 10. The wavelength stabilizing arrangement 140A in the light injection unit 20-4 is realized by the narrow-band-pass filter 141, the condensing lens 144, the half mirror 145, and the collimator lens 146.

The condensing lens 144 and the half mirror 145 constitute an optical system for realizing optical feedback. The half mirror 145 is arranged at the focal position of the condensing lens 144. A portion of the measurement light L1 is reflected by the half mirror 145, and fed back to the semiconductor laser 100 through the narrow-band-pass filter 141. When the portion of the measurement light L1 is fed back through the narrow-band-pass filter 141, the portion of the measurement light L1 undergoes wavelength selection, so that the oscillation wavelength of the semiconductor laser 100 is locked at the selected wavelength of the narrow-band-pass filter 141.

Sixth Embodiment

A sensing system according to the sixth embodiment of the present invention is explained below with reference to FIG. 8, which is a schematic diagram illustrating a light injection unit 20-5 used in the sensing system according to the sixth embodiment.

Figure 8:
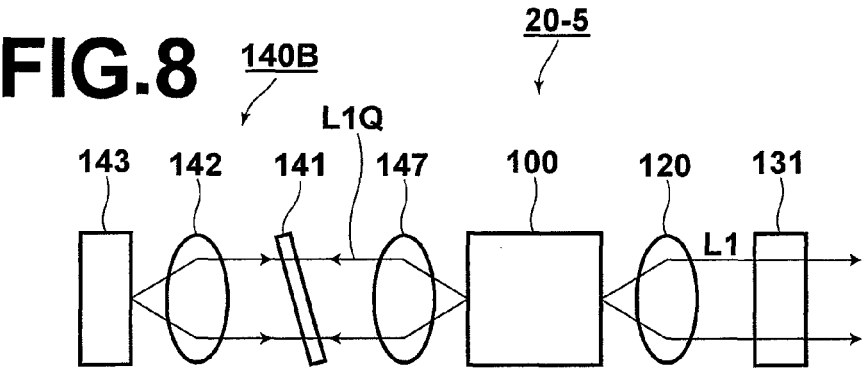
FIG. 8 is a schematic diagram illustrating a light injection unit in a sensing system according to a sixth embodiment of the present invention.

In the light injection unit 20-5 illustrated in FIG. 8, the collimator lens 120 and the half-wavelength plate 131 are arranged on the forward side of the semiconductor laser 100, and a collimator lens 147, a narrow-band-pass filter 141, a condensing lens 142, and a mirror 143 are arranged in this order in the optical path of the light emitted backward from the semiconductor laser 100 (backward emission light L1Q). The wavelength stabilizing arrangement 140B in the light injection unit 20-5 is realized by the collimator lens 147, the narrow-band-pass filter 141, the condensing lens 142, and the mirror 143. The collimator lens 147 collimates the backward emission light L1Q, and the condensing lens 142 condenses the backward emission light L1Q after the backward emission light L1Q passes through the narrow-band-pass filter 141. The mirror 143 is arranged at the focal position of the condensing lens 142. The condensing lens 142 and the mirror 143 constitute an optical system for realizing optical feedback, and the narrow-band-pass filter 141 realizes a wavelength selection means. That is, when the backward emission light L1Q passes through the narrow-band-pass filter 141, the backward emission light L1Q undergoes wavelength selection. Then, the backward emission light L1Q is reflected by the mirror 143 so that the reflected backward emission light L1Q retraces the optical path of the backward emission light L1Q and is fed back to the semiconductor laser 100. Thus, the oscillation wavelength of the semiconductor laser 100 is locked at the selected wavelength of the narrow-band-pass filter 141.

Seventh Embodiment

A sensing system according to the seventh embodiment of the present invention is explained below with reference to FIG. 9, which is a schematic diagram illustrating a light injection unit 20-6 used in the sensing system according to the seventh embodiment.

Figure 9:
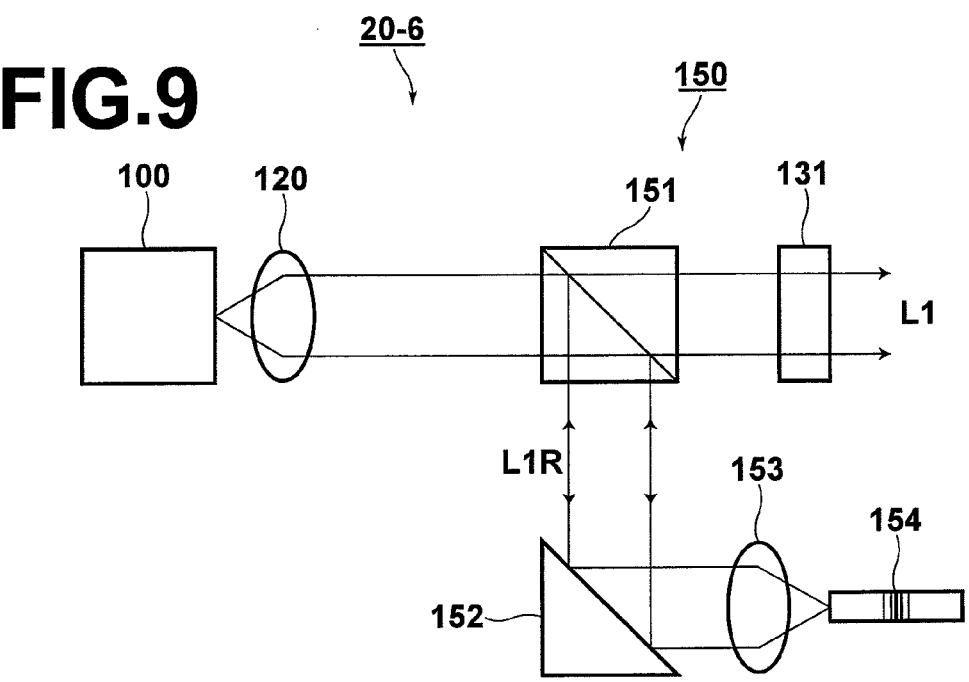
FIG. 9 is a schematic diagram illustrating a light injection unit in a sensing system according to a seventh embodiment of the present invention.

In the light injection unit 20-6 illustrated in FIG. 9, a beam splitter 151, a mirror 152, a condensing lens 153, and a reflective fiber grating 154, which constitute a wavelength stabilizing arrangement 150, are arranged.

The reflective fiber grating 154 is an optical fiber in which a high-refractive-index core is covered by a cladding, and the core includes a plurality of refractive-index changed portions formed at regular intervals. For example, the reflective fiber grating 154 can be made of an optical fiber designed for use in optical communication and constituted by a cladding having an outside diameter of 125 micrometers and a core having a diameter of approximately 10 micrometers, by generating two-beam interference fringes of excimer laser light in the ultraviolet wavelength range so as to change (increase) refractive indexes of a plurality of portions which are exposed to the two-beam interference light. It is considered that germanium dioxide doped in the core is chemically changed by the exposure to the ultraviolet light, so that the refractive indexes of the plurality of portions of the core are changed. The plurality of portions in which the refractive indexes are changed realize a grating having a specific pitch along the direction of light which propagates through the reflective fiber grating 154.

In the light injection unit 20-6 illustrated in FIG. 9, the measurement light L1 emitted from the semiconductor laser 100 enters the beam splitter 151, in which a portion L1R of the measurement light L1 branches off toward the mirror 152. The mirror 152 reflects the light beam L1R toward the condensing lens 153, and the condensing lens 153 condenses the reflected light beam L1R so that the condensed light beam L1R enters the reflective fiber grating 154. The reflective fiber grating 154 is arranged so that an end of the reflective fiber grating 154 is located at the focal position of the condensing lens 153. Then, the light beam L1R propagates through the reflective fiber grating 154. At this time, the grating realized in the reflective fiber grating 154 diffracts and reflects only a component of the light beam L1R having a specific wavelength corresponding to the pitch of the grating, so that the component having the specific wavelength is fed back to the semiconductor laser 100 through the mirror 152 and the beam splitter 151. Thus, the oscillation wavelength of the semiconductor laser 100 is locked at the selected wavelength of the reflective fiber grating 154.

Eighth Embodiment

A sensing system according to the eighth embodiment of the present invention is explained below with reference to FIG. 10, which is a schematic diagram illustrating a light injection unit 20-7 used in the sensing system according to the eighth embodiment.

Figure 10:
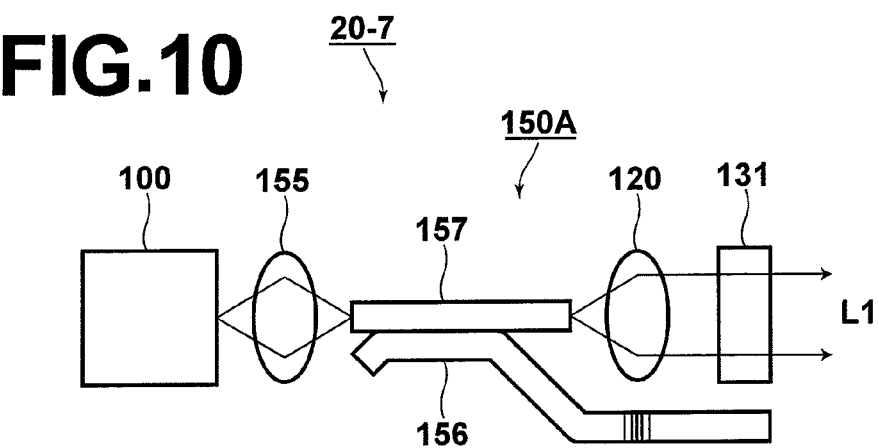
FIG. 10 is a schematic diagram illustrating a light injection unit in a sensing system according to an eighth embodiment of the present invention.

In the light injection unit 20-7 illustrated in FIG. 10, a condensing lens 155, a first optical fiber 156, and a second optical fiber 157, which constitute a wavelength stabilizing arrangement 150A, are arranged.

The condensing lens 155 condenses the light beam L1 emitted from the semiconductor laser 100. The first optical fiber 156 contains a plurality of refractive-index changed portions which are similar to those formed in the reflective fiber grating 154 in the seventh embodiment. The second optical fiber 157 is coupled to the first optical fiber 156 so as to form a fiber coupler.

The light beam L1 condensed by the condensing lens 155 enters the second optical fiber 157 from an end of the second optical fiber 157, and propagates in the second optical fiber 157, and is split into two portions. The first portion of the light beam L1 propagates through the second optical fiber 157, and is output from the other end of the second optical fiber 157 for use as the measurement light. The second portion of the light beam L1 propagates from the second optical fiber 157 to the first optical fiber 156 through the coupling of the first and second optical fibers 156 and 157, and propagates in the first optical fiber 156. Then, a component of the second portion of the light beam L1 having a specific wavelength is diffracted and reflected by the grating realized by the plurality of refractive-index-varied portions. The reflected component of the second portion of the light beam L1 is fed back to the semiconductor laser 100 through the second optical fiber 157 and the condensing lens 155. Thus, the oscillation wavelength of the semiconductor laser 100 is locked at the wavelength selected by the first optical fiber 156.

Ninth Embodiment

A sensing system according to the ninth embodiment of the present invention is explained below with reference to FIG. 11, which is a schematic diagram illustrating a light injection unit 20-8 used in the sensing system according to the ninth embodiment.

Figure 11:
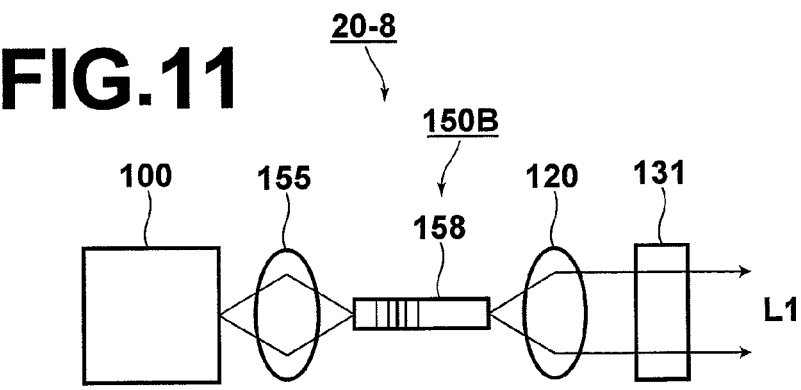
FIG. 11 is a schematic diagram illustrating a light injection unit in a sensing system according to a ninth embodiment of the present invention.

In the light injection unit 20-8 illustrated in FIG. 11, a condensing lens 155 and a partially-reflective fiber grating 158, which constitute a wavelength stabilizing arrangement 150B, are arranged.

The condensing lens 155 condenses the laser beam L1 emitted from the semiconductor laser 100 so that the condensed light beam L1 enters the partially-reflective fiber grating 158. The partially-reflective fiber grating 158 is arranged so that an end of the partially-reflective fiber grating 158 is located at the focal position of the condensing lens 155.

The partially-reflective fiber grating 158 has a substantially similar structure to the reflective fiber grating 154 in the seventh embodiment, and partially diffracts and reflects only a portion of the laser beam L1 which has a specific wavelength corresponding to the pitch of the grating so that the portion of the laser beam L1 having the specific wavelength is fed back to the semiconductor laser 100. Thus, the oscillation wavelength of the semiconductor laser 100 is locked at the wavelength selected by the partially-reflective fiber grating 158. In addition, the remaining portion of the laser beam L1 propagates through the partially-reflective fiber grating 158, and is outputted from the other end face of the partially-reflective fiber grating 158 for use as the measurement light L1.

Tenth Embodiment

A sensing system according to the tenth embodiment of the present invention is explained below with reference to FIG. 12, which is a schematic diagram illustrating a light injection unit 20-9 used in the sensing system according to the tenth embodiment.

Figure 12:
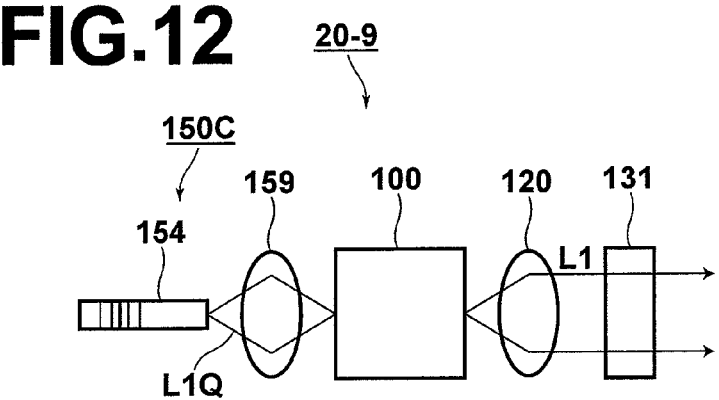
FIG. 12 is a schematic diagram illustrating a light injection unit in a sensing system according to a tenth embodiment of the present invention.

In the light injection unit 20-9 illustrated in FIG. 12, a condensing lens 159 and a partially-reflective fiber grating 154, which constitute a wavelength stabilizing arrangement 150C, are arranged.

The condensing lens 159 condenses backward emission light L1Q emitted backward from the semiconductor laser 100 so that the condensed backward emission light L1Q enters the partially-reflective fiber grating 154. The partially-reflective fiber grating 154 is arranged so that an end of the partially-reflective fiber grating 154 is located at the focal position of the condensing lens 159.

The partially-reflective fiber grating 154 in the tenth embodiment has substantially the same structure as the reflective fiber grating 154 in the seventh embodiment, and partially diffracts and reflects only a component of the backward emission light L1Q which has a specific wavelength corresponding to the pitch of the grating so that the component of the backward emission light L1Q having the specific wavelength is fed back to the semiconductor laser 100. Thus, the oscillation wavelength of the semiconductor laser 100 is locked at the wavelength selected by the partially-reflective fiber grating 154.

Eleventh Embodiment

A sensing system according to the eleventh embodiment of the present invention is explained below with reference to FIG. 13, which is a schematic diagram illustrating a sensing system 201 according to the eleventh embodiment.

The sensing system 201 comprises a sensing element 210, a specimen cell 215, a light injection unit 20-10, a light detection unit 30-1, and a calculation unit 240.

When measurement light L1 for measurement is injected onto the sensing element 210, the sensing element 210 outputs output light L2 having a physical characteristic which depends on a specimen 217. The specimen cell 215 contains the sensing element 210 and the specimen 217, and the light injection unit 20-10 injects the measurement light L1 onto the sensing element 210, where the measurement light L1 is composed of measurement light L1a and measurement light L1b having different wavelengths. The light detection unit 30-1 detects the intensities of the output light L2a and output light L2b corresponding to the measurement light L1a and the measurement light L1b at the different wavelengths, respectively, and outputs detection signals Sa and Sb respectively indicating the detected intensities of the output light L2a and output light L2b. The calculation unit 240 obtains a difference signal Ss indicating the difference between the detection signals Sa and Sb.

Similar to the sensing element 10 used in the first embodiment, the sensing element 210 has a structure constituted by a first reflector 211, a transparent body 212, and a second reflector 213. The first reflector 211 is arranged on the light-injection side (the lower side in FIG. 13) of the transparent body 212, and the second reflector 213 is arranged on the opposite side of the transparent body 212. The first reflector 211 is partially transparent and partially reflective, and the second reflector 213 is completely reflective.

The specimen cell 215 contains the sensing element 210 and the specimen 217, and the sensing element 210 is permanently or detachably fixed in the specimen cell 215 by using a fixing structure (not shown) so that the first reflector 211 and the second reflector 213 are in contact with the specimen 217.

Figure 13:
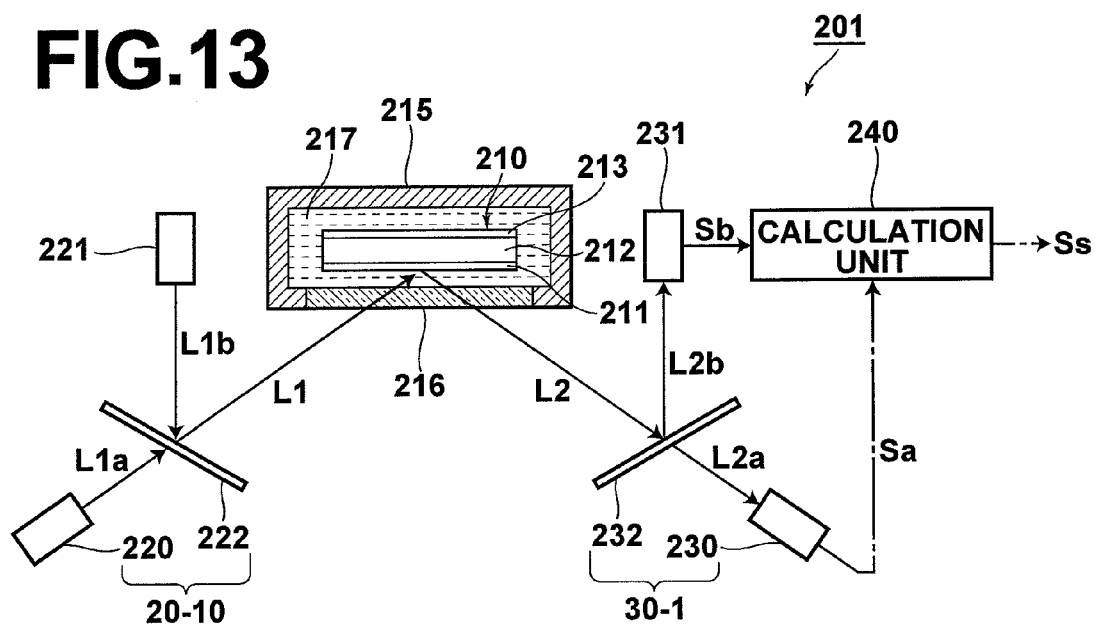
FIG. 13 is a schematic diagram illustrating a sensing system according to an eleventh embodiment of the present invention.

As illustrated in FIG. 13, the specimen cell 215 is constituted by a cell body and a transparent window 216. The cell body is formed of a nontransparent material such as metal in such a shape that the specimen cell 215 has a window and can be filled with the specimen 217, and the transparent window panel 216 is transparent to the measurement light L1 and the output light L2 and inserted into the window of the cell body. The window panel 216 and the sensing element 210 are arranged so that the first reflector 211 faces the window panel 216.

The light injection unit 20-10 is constituted by a first laser-light source 220, a second laser-light source 221, and a dichroic mirror 222. The first laser-light source 220 emits the measurement light L1a having the wavelength λ1, and the second laser-light source 221 emits the measurement light L1b having the wavelength λ2. The dichroic mirror 222 is arranged to transmit the measurement light L1a and reflect the measurement light L1b, so that the measurement light L1a and the measurement light L1b are optically combined into the measurement light L1 in the form of a narrow parallel beam, which is injected onto the sensing element 210.

The light detection unit 30-1 is constituted by a first optical detector 230, a second optical detector 231, and a dichroic mirror 232. The dichroic mirror 232 is arranged to transmit the output light L2a and reflect the output light L2b when the output light L2 (in which the output light L2a and the output light L2b are optically combined) is incident on the dichroic mirror 232. The first optical detector 230 detects the output light L2a corresponding to the measurement light L1a having the wavelength λ1, and the second optical detector 231 detects the output light L2b corresponding to the measurement light L1b having the wavelength λ2. Thus, the dichroic mirror 232 splits the output light L2 into the output light L2a and the output light L2b. The output light L2a and the output light L2b are respectively detected by the first optical detector 230 and the second optical detector 231, which are, for example, realized by photodiodes.

In addition, a light-guiding optical system constituted by one or more of collimator lenses, condensing lenses, and the like may be provided with each of the light injection unit 20-10 and the light detection unit 30-1 as needed.

In the sensing system 201 according to the eleventh embodiment, the measurement light L1a and the measurement light L1b, which have different wavelengths, are injected onto the sensing element 210, the intensities of the output light L2a and the output light L2b respectively corresponding to the measurement light L1a and the measurement light L1b are detected by the first optical detector 230 and the second optical detector 231, and the difference signal Ss indicating the difference between the detection signals Sa and Sb outputted from the first optical detector 230 and the second optical detector 231 is obtained. Since the wavelength dependence of the absorption in the sensing element 210 varies with the specimen 217 as mentioned before, the above difference signal Ss also varies with the specimen 217. Therefore, it is possible to quantitatively analyze the specimen 217 on the basis of the difference signal Ss. In addition, since noise components superimposed on the detection signals Sa and Sb can be cancelled by obtaining the difference signal Ss, the signal-to-noise ratio of the difference signal Ss is high, so that it is possible to perform the analysis with sufficiently high precision.

As mentioned before, the sensing system 201 according to the eleventh embodiment can analyze the refractive index and/or concentration of the specimen, and identify the specimen by analyzing the refractive index of the specimen. In addition, the sensing system 201 can determine presence or absence of a specific material in the specimen, or analyze the quantity of the specific material contained in the specimen, by fixing a specific binding material (which can be specifically bound to the specific material) to a surface or surfaces of the sensing element 210 which are to be arranged in contact with the specimen, arranging the surface or surfaces in contact with the specimen, injecting the measurement light L1 onto the sensing element 210, and detecting the output light L2 outputted from the sensing element 210. After the output light L2 is measured as above, it is possible to reuse the sensing element 210 by separating the specific binding material bound to the specific material and the specific binding material fixed to the sensing element 210 in the manners as disclosed in PCT Japanese Publication Nos. 11 (1999)-512518, 2002-517720 and 2003-527606.

In the sensing system 201 according to the eleventh embodiment using the reflective sensing element 210 explained before, it is preferable that the light detection unit 30-1 detect the output light L2 by receiving only nonregular-reflection components such as scattered light included in the output light L2 outputted from the first reflector 211. Since the intensity of the regular-reflection components of the output light L2 is too high, there is a possibility that the characteristic which is required to be detected cannot be satisfactorily detected on the basis of the intensity of the regular-reflection components. However, in the case where the weak light such as the scattered light is detected, the analysis can be performed with higher precision. In addition, for a similar reason, it is preferable that the light injection unit 20-10 be arranged at such a position that the light injection unit 20-10 can inject the measurement light L1 in a direction which is not perpendicular to the incident plane of the sensing element 210.

The construction of the specimen cell 215 used in the sensing system 201 is not limited to the aforementioned construction, and may be arranged in various manners. For example, in the case where a partially-transparent, partially-reflective sensing element or a reflective sensing element which outputs the output light L2 from the first reflector 211 is used, the specimen cell 215 may be arranged so that only the second reflector 213 is in contact with the specimen 217.

Twelfth Embodiment

A sensing system according to the twelfth embodiment of the present invention is explained below with reference to FIG. 14, which is a schematic diagram illustrating a sensing system 202 according to the twelfth embodiment.

Figure 14:
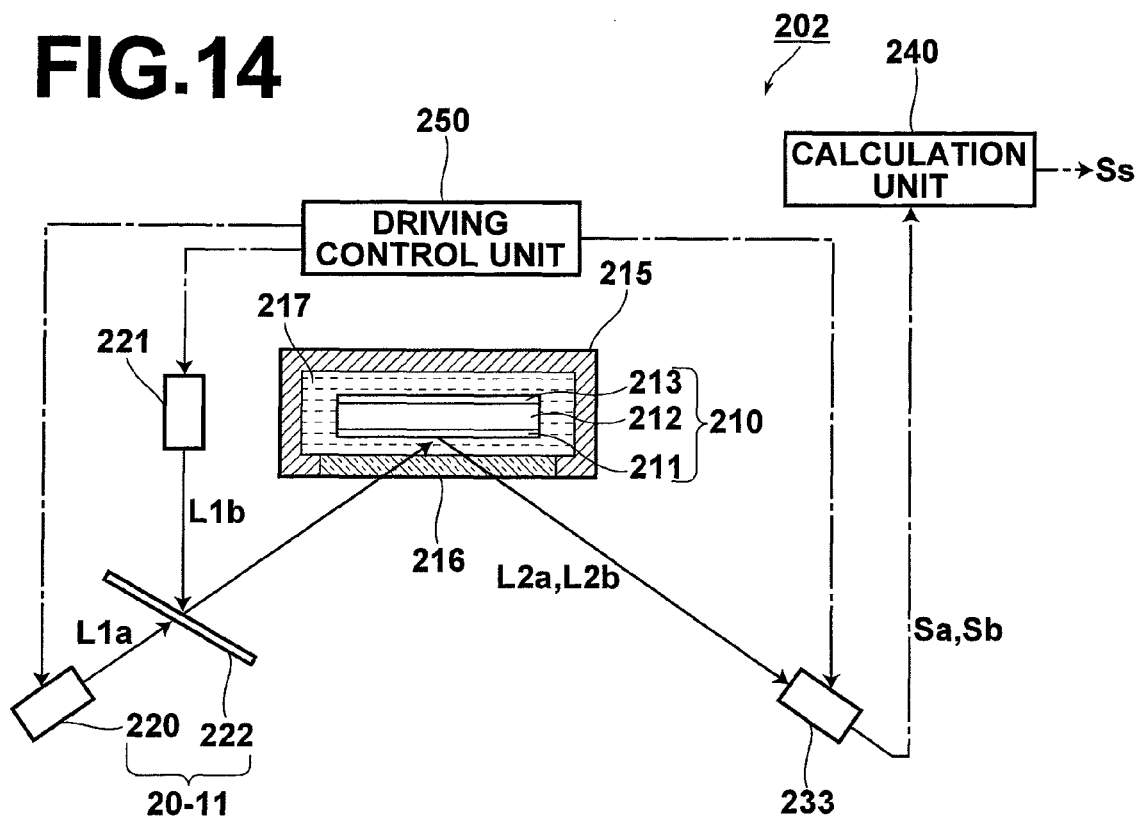
FIG. 14 is a schematic diagram illustrating a sensing system according to a twelfth embodiment of the present invention.

The sensing system 202 illustrated in FIG. 14 is different from the sensing system 201 illustrated in FIG. 13 as follows.

In the sensing system 202, a driving control unit 250 is provided for controlling the first laser-light source 220 and the second laser-light source 221 so that activation of the second laser-light source 221 is started when a predetermined time elapses after activation of the first laser-light source 220 is completed (stopped). Therefore, injection of the measurement light L1b having the wavelength $\lambda 2$ onto the sensing element 210 is started when the predetermined time elapses after injection of the measurement light L1a having the wavelength $\lambda 1$ is completed.

In addition, the light injection unit 20-11 is realized by only a single optical detector 233, the operation of which is also controlled by the driving control unit 250. That is, the optical detector 233 is activated for detection of the output light L2a and the output light L2b in synchronization with the activation of the first optical detector 230 and the second optical detector 231, respectively, so that the optical detector 233 outputs the detection signal Sa indicating the intensity of the output light L2a when the first laser-light source 220 is activated, and the detection signal Sb indicating the intensity of the output light L2b when the second laser-light source 221 is activated.

The detection signals Sa and Sb outputted at intervals from the optical detector 233 are supplied to the calculation unit 240 The calculation unit 240 temporarily stores the detection signals Sa and Sb in an internal memory (not shown), obtains the difference between the detection signals Sa and Sb, and outputs the difference signal Ss.

Since the analysis is performed by using the difference signal Ss obtained as above in the sensing system 202 according to the twelfth embodiment, it is also possible to achieve similar advantages to the eleventh embodiment.

Other Sensing Elements

In the sensing systems according to the present invention, the sensing element is not limited to the sensing elements 10 or 210 used in the above embodiments, and various sensing element can be used. For example, the sensing element as illustrated in FIGS. 15A to 17 may be used. In the following explanations, only the differences from the sensing elements 10 or 210 are indicated.

Figure 15A:
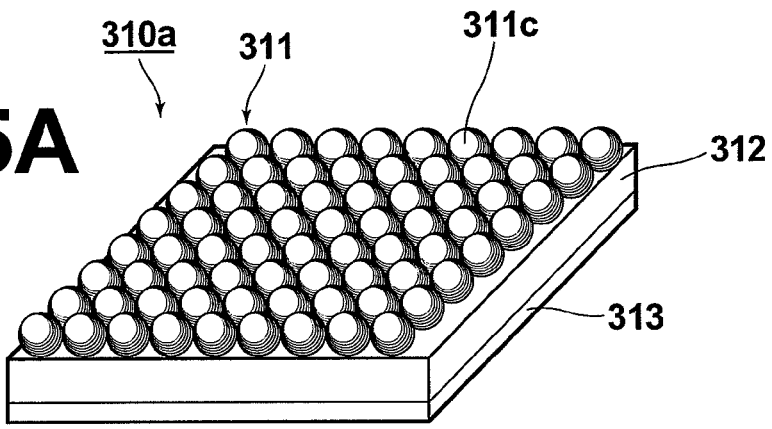
FIG. 15A is a perspective view of a first additional example of a sensing element which can be used in a sensing system according to the present invention.
Figure 15B:
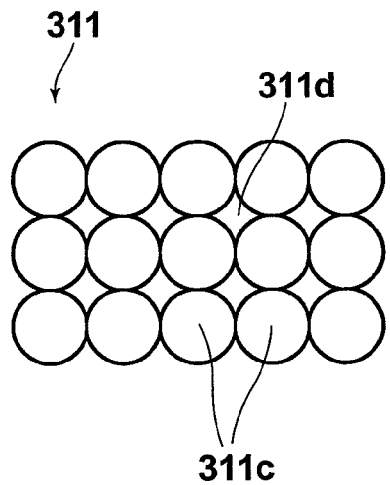
FIG. 15B is a top view of the sensing element of FIG. 15A.

FIGS. 15A and 15B are perspective and top views of a first additional example 310a of the sensing element which can be used in the sensing systems according to the present invention.

As illustrated in FIGS. 15A and 15B, the sensing element 310a has a structure constituted by a first reflector 311, a transparent body 312, and a second reflector 313. The first reflector 311 is arranged on the light-injection side (the upper side in FIG. 15A) of the transparent body 312, and the second reflector 313 is arranged on the opposite side of the transparent body 312. The first reflector 311 is partially transparent and partially reflective, and the second reflector 313 is completely reflective. The sensing element 310a is different from the sensing element 10 used in the first embodiment in that the first reflector 311 is realized by a metal layer which is formed of a plurality of metal particles 311c having approximately identical diameters, and the metal particles 311c are regularly arrayed in a matrix arrangement on a surface of the transparent body 312 and fixed to the surface, while a reflective material is formed in a pattern in the metal layer realizing the first reflector 11 in the sensing element 10. The material of which the first reflector 311 is formed is not specifically limited, and the first reflector 311 may be formed of a similar metal to the first reflector 11 in the sensing element 10.

Although the first reflector 311 is formed of metal, which is reflective, there are gaps 311d between the metal particles. Therefore, the first reflector 311 is partially transparent to light. That is, the first reflector 311 is partially transparent and partially reflective. The diameters and the array pitches of the metal particles 311c are designed to be smaller than the wavelength or wavelengths of the measurement light L1. That is, the first reflector 311 has a structure with protrusions and recesses finer than the wavelength or wavelengths of the measurement light L1. Therefore, the first reflector 311 also has the electromagnetic shield effect as the metal mesh, so that the first reflector 311 becomes a thin film which is partially transparent and partially reflective. Thus, even in the cases where the sensing element 310a is used instead of the sensing element 10 or 210 in the sensing systems according to the first to twelfth embodiments of the present invention, the advantages of the first to twelfth embodiments are not substantially changed.

Figure 16:
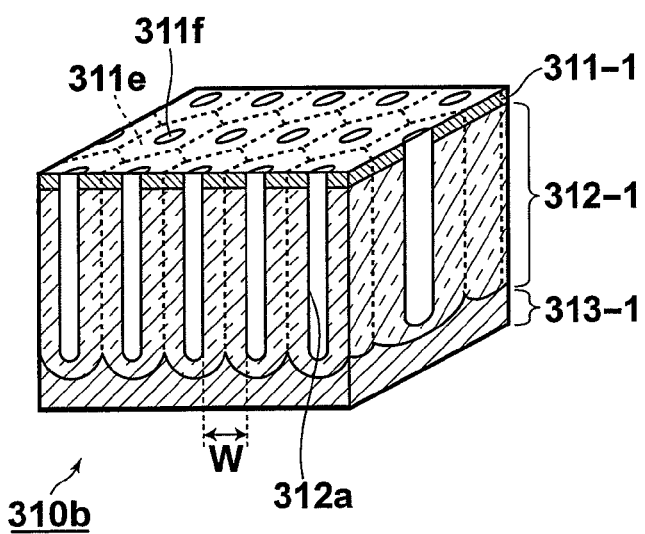
FIG. 16 is a perspective view of a second additional example of a sensing element which can be used in a sensing system according to the present invention.

FIG. 16 is a perspective view of a second additional example 310b of the sensing element which can be used in a sensing system according to the present invention.

As illustrated in FIG. 16, the sensing element 310b also has a structure constituted by a first reflector 311-1, a transparent body 312-1, and a second reflector 313-1. The first reflector 311-1 is arranged on the light-injection side (the upper side in FIG. 16) of the transparent body 312-1, and the second reflector 313-1 is arranged on the opposite side of the transparent body 312-1. The first reflector 311-1 is partially transparent and partially reflective, and the second reflector 313-1 is completely reflective. However, the first reflector 311-1, the transparent body 312-1, and the second reflector 313-1 are different from the first reflector, the transparent body, and the second reflector constituting the sensing elements 10, 210, or 310a, which are explained before.

In the sensing element 310b, the transparent body 312-1 is formed of metal oxide (e.g., $Al_2O_3$) which is obtained by anodic oxidation of a portion of a body of metal (e.g., aluminum), and the second reflector 313-1 is realized by the remaining portion of the metal which is not anodically oxidized. The second reflector 313-1 is completely reflective.

The transparent body 312-1 is a transparent microporous body. In the transparent microporous body, a plurality of micropores 312a approximately straightly extending from a first surface on the first-reflector side to vicinities of a second surface on the second-reflector side. That is, the micropores 312a are open on the first-reflector side, and closed on the second-reflector side. The micropores 312a have diameters smaller than the wavelength or wavelengths of the measurement light L1, and are approximately regularly arranged with array pitches W smaller than the wavelength or wavelengths of the measurement light L1.

The first reflector 311-1 is a metal layer formed on the first surface of the transparent body 312-1 by evaporation or the like. Since the micropores 312a are open on the first-reflector side, the metal is evaporated on the areas of the first surface other than the openings of the micropores 312a, so that the first reflector 311-1 is formed of equilateral hexagonal metal sections 311e closely arranged to cover the first surface of the transparent body 312-1, and micropores 311f are located approximately at the centers of the equilateral hexagonal metal sections 311e, respectively. Since the micropores 311f in the first reflector 311-1 are arranged in the same pattern as the micropores 312a in the transparent body 312-1, the micropores 311f have diameters smaller than the wavelength or wavelengths of the measurement light L1, and are approximately regularly arranged with array pitches smaller than the wavelength or wavelengths of the measurement light L1.

Although the first reflector 311-1 is formed of metal (which is reflective), the micropores 311f are distributed over the entire area. Therefore, the first reflector 311-1 is partially transparent to light. That is, the first reflector 311-1 is partially transparent and partially reflective. Since the first reflector 311-1 has a structure with protrusions and recesses finer than the wavelength or wavelengths of the measurement light L1, the first reflector 311-1 also has the electromagnetic shield effect as the metal mesh, so that the first reflector 311-1 becomes a thin film which is partially transparent and partially reflective. Thus, even in the cases where the sensing element 310b is used instead of the sensing element 10 or 210 in the sensing systems according to the first to twelfth embodiments of the present invention, the advantages of the first to twelfth embodiments are not substantially changed.

The material from which the transparent body 312-1 is made is not limited to aluminum, and may be any metal which can be anodically oxidized and the anodic oxide of which is transparent to light. For example, the transparent body 312-1 may be made from Ti, Ta, Hf, Zr, Si, In, Zn, or the like. Further, the transparent body 312-1 may be made from more than one metal which can be anodically oxidized.

Although the second reflector 313-1 is completely reflective in the above sensing element 310b, alternatively, it is possible to make the second reflector 313-1 partially transparent and partially reflective, for example, by forming the micropores 312a through the entire thickness of the transparent body 312-1, and forming the second reflector 313-1 on only the areas of the second surface of the transparent body 312-1 other than the openings of the micropores 312a. In this case, the second reflector 313-1 has micropores and becomes partially transparent and partially reflective as the first reflector 311-1. For example, the transparent body 312-1 having the micropores 312a formed through the entire thickness of the transparent body 312-1 can be formed by anodically oxidizing the entire body of the metal from which the transparent body 312-1 and the first reflector 311-1 is to be formed, or anodically oxidizing a portion of the body of the metal and removing the remaining portion of the metal which is not anodically oxidized and vicinities of the remaining portion.

Figure 17:
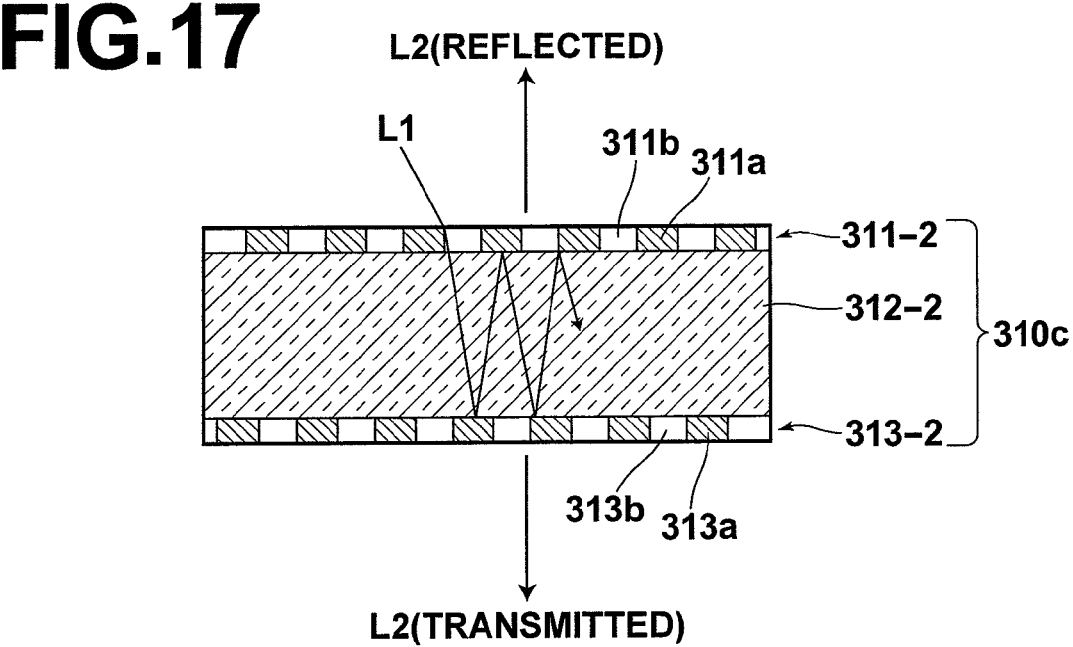
FIG. 17 is a cross-sectional view of a third additional example of a sensing element which can be used in a sensing system according to the present invention.

FIG. 17 is a cross-sectional view of a third additional example 310c of the sensing element which can be used in a sensing system according to the present invention.

As illustrated in FIG. 17, the sensing element 310c also has a structure constituted by a first reflector 311-2, a transparent body 312-2, and a second reflector 313-2. The first reflector 311-2 is arranged on the light-injection side (the upper side in FIG. 17) of the transparent body 312-2, and the second reflector 313-2 is arranged on the opposite side (the lower side in FIG. 17) of the transparent body 312-2. The first reflector 311-2 is partially transparent and partially reflective. However, the sensing element 310c is different from the sensing element 10 used in the first embodiment in that both of the first reflector 311-2 and the second reflector 313-2 are realized by partially transparent and partially reflective metal layers, while the second reflector 13 in the sensing element 10 is realized by the metal layer covering the entire bottom surface of the transparent body 12 and is completely reflective. In the sensing element 310c, each of the first reflector 311-2 and the second reflector 313-2 is formed in a similar manner to the first reflector 11 in the sensing element 10. Specifically, the second reflector 313-2 is formed by arranging fine metal wires 313a and gaps 313b on the bottom surface of the transparent body 312-2 in a regular grid pattern. The first reflector 311-2 is formed similarly with wires 311a and gaps 311b. In the sensing element 310c, both of the first reflector 311-2 and the second reflector 313-2 have a structure with protrusions and recesses finer than the wavelength or wavelengths of the measurement light L1, the average complex refractive index of a reflector sensitively varies with the specimen when either of the first reflector 311-2 and the second reflector 313-2 is arranged in contact with the specimen. Thus, even in the cases where the sensing element 310c is used instead of the sensing element 10 or 210 in the sensing systems according to the first to twelfth embodiments of the present invention, the advantages of the first to twelfth embodiments are not substantially changed.

Further, the structures of the first and second reflectors or the combination of the structures of the first and second reflectors can be modified within the scope of the present invention when necessary. For example, the first and second reflectors can be realized by combining the structures of the first and second reflectors in the sensing elements 10, 310a, 310b, and 310c.

In the case where the second reflector is also partially transparent and partially reflective, it is possible to detect the output light L2 from the second-reflector side of the sensing element. In this case, the position of the transparent window, the arrangement of the light detection unit, and the like can be modified according to the position from which the output light L2 is outputted.

The invention claimed is:

1. A sensing system comprising:
    a sensing element which outputs light having a physical characteristic varying with a specimen, in response to injection of light onto the sensing element;
    a light injection unit which injects laser light as first light onto said sensing element, and has a wavelength stabilizing arrangement stabilizing an oscillation wavelength of the laser light by use of a wavelength selector built in the wavelength stabilizing arrangement; and
    a light detection unit which detects a physical characteristic of second light which is outputted from said sensing element in response to injection of said first light onto the sensing element;
    wherein said sensing element includes,
        a transparent body,
        a first reflector which is partially transparent and partially reflective, and is arranged on a first side of the transparent body from which said first light is injected and said second light is outputted, and
        a second reflector which is completely reflective, or partially transparent and partially reflective, and is arranged on a second side of the transparent body opposite to said first side;
    at least one of said first reflector and said second reflector is arranged in contact with the specimen, and has an average complex refractive index which varies with the specimen; and
    said sensing element exhibits an absorption characteristic that light injected onto the sensing element is selectively absorbed at a specific wavelength according to average complex refractive indexes which said first reflector and said second reflector respectively have and an average complex refractive index and a thickness which said transparent body has, and outputs light in which said absorption characteristic is reflected, from at least one of said first reflector and said second reflector.

2. The system according to claim 1, wherein the light detection unit is able to detect the physical characteristics of the second light even in absence of a polarizing element disposed between the light injection unit and the light detection unit.

3. A sensing system comprising:
    a sensing element which outputs light having a physical characteristic varying with a specimen, in response to injection of light onto the sensing element;
    a light injection unit which injects light with two or more wavelengths onto said sensing element, where the light injected by the light injection unit includes first light having a first wavelength and second light having a second wavelength different from the first wavelength;
    a light detection unit which detects a first intensity of third light which is outputted from said sensing element in response to injection of said first light onto the sensing element, and a second intensity of fourth light which is outputted from said sensing element in response to injection of said second light onto the sensing element; and
    a calculation unit which obtains a difference between said first intensity and said second intensity;
    wherein said sensing element includes,
        a transparent body,
        a first reflector which is partially transparent and partially reflective, and is arranged on a first side of the transparent body from which said first light and said second light are injected, and
        a second reflector which is completely reflective, or partially transparent and partially reflective, and is arranged on a second side of the transparent body opposite to said first side;
    at least one of said first reflector and said second reflector is arranged in contact with the specimen, and has an average complex refractive index which varies with the specimen; and
    said sensing element exhibits an absorption characteristic that light injected onto the sensing element is selectively absorbed at a specific wavelength according to average complex refractive indexes which said first reflector and said second reflector respectively have and an average complex refractive index and a thickness which said transparent body has, and outputs light in which said absorption characteristic is reflected, from at least one of said first reflector and said second reflector.

* * * * *